(12) United States Patent
Uber, III et al.

(10) Patent No.: US 6,889,074 B2
(45) Date of Patent: May 3, 2005

(54) PATIENT SPECIFIC DOSING CONTRAST DELIVERY SYSTEMS AND METHODS

(75) Inventors: Arthur E. Uber, III, Pittsburgh, PA (US); Alan D. Hirschman, Glenshaw, PA (US); Thomas R. Welch, Gibsonia, PA (US); Rosemary Almon-Martin, Saxonburg, PA (US)

(73) Assignee: Medrad, Inc., Indianola, PA (US)

( * ) Notice: Subject to any disclaimer, the term of this patent is extended or adjusted under 35 U.S.C. 154(b) by 372 days.

(21) Appl. No.: 09/749,894

(22) Filed: Dec. 29, 2000

(65) Prior Publication Data

US 2001/0056233 A1 Dec. 27, 2001

Related U.S. Application Data

(62) Division of application No. 09/197,773, filed on Nov. 23, 1998, now Pat. No. 6,385,483, which is a division of application No. 08/309,820, filed on Sep. 21, 1994, now Pat. No. 5,840,026.

(51) Int. Cl.[7] ................................................ A61B 6/00
(52) U.S. Cl. ..................... 600/431; 600/432; 604/30; 604/31; 604/33; 604/36; 604/67; 604/246
(58) Field of Search ..................... 600/431, 432–435; 604/30, 31, 33, 27, 28, 246, 65, 67, 36

(56) References Cited

U.S. PATENT DOCUMENTS

| | | |
|---|---|---|
| 3,349,713 A | 10/1967 | Fassbender |
| 3,523,523 A | 8/1970 | Reich |
| 3,623,474 A | 11/1971 | Heilman et al. |
| 3,701,345 A | 10/1972 | Heilman et al. |
| 3,755,655 A | 8/1973 | Sewecal |
| 3,793,600 A | 2/1974 | Groubard |
| 3,812,843 A | 5/1974 | Wjutten et al. |
| 3,895,220 A | 7/1975 | Nelson et al. |

(Continued)

FOREIGN PATENT DOCUMENTS

| | | |
|---|---|---|
| CA | 2045070 | 2/1992 |
| DE | 3 726 452 | 2/1989 |
| DE | 41 21 568 A1 | 10/1992 |
| DE | 4121568 | 10/1992 |
| EP | 0 337 924 | 10/1989 |
| EP | 0343501 | 11/1989 |
| EP | 0 600 448 | 6/1994 |
| EP | 0 650 739 | 5/1995 |
| FR | 2493708 | 5/1982 |
| FR | 2561949 | 10/1985 |
| GB | 2 207 749 | 2/1989 |
| GB | 2252656 | 8/1992 |
| WO | WO80/01754 | 9/1980 |
| WO | WO85/00292 | 1/1985 |
| WO | WO94/15664 | 7/1994 |

OTHER PUBLICATIONS

Mark V and Mark V Plus Injection Systems, Operation Manual KMP 805P, Rev. B, (pp. 1–22 to 1–23; 3–1 to 3–21 14–1 to 14–3) (1990).

"Disposable Low–Cost Catheter Tip Sensor Measures Blood Pressure During Surgery," Sensor, (Jul. 1989).

*Primary Examiner*—Ruth S. Smith
(74) *Attorney, Agent, or Firm*—Pillsbury Winthrop LLP

(57) ABSTRACT

This invention relates generally to the field of medical devices for delivering contrast media during medical diagnostic and therapeutic imaging procedures and more particularly, this invention relates to improved contrast media delivery systems and methods of use which allow adjustment of contrast media concentration and injection parameters either before or during an injection procedure to provide patient specific dosing of contrast media, thus decreasing the waste and cost of these procedures while increasing their efficiency.

59 Claims, 16 Drawing Sheets

U.S. PATENT DOCUMENTS

| | | |
|---|---|---|
| 3,898,983 A | 8/1975 | Elam |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,038,981 A | 8/1977 | LeFevre et al. |
| 4,151,845 A | 5/1979 | Clemens |
| 4,187,057 A | 2/1980 | Xanthopoulos |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,280,494 A | 7/1981 | Cosgrove, Jr. et al. |
| 4,319,568 A | 3/1982 | Tregoning |
| 4,340,153 A | 7/1982 | Spivey |
| 4,392,849 A | 7/1983 | Petre et al. |
| 4,396,385 A | 8/1983 | Kelly et al. |
| 4,434,822 A | 3/1984 | Bellamy et al. |
| 4,447,230 A | 5/1984 | Gula et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,544,949 A | 10/1985 | Kurihara |
| 4,551,133 A | 11/1985 | Zegers de Beyl et al. |
| 4,559,036 A | 12/1985 | Wunsch |
| 4,563,175 A | 1/1986 | LaFond |
| 4,585,009 A | 4/1986 | Barker et al. |
| 4,610,670 A | 9/1986 | Spencer |
| 4,610,790 A | 9/1986 | Reti et al. |
| 4,633,307 A | 12/1986 | Honda |
| 4,634,426 A | 1/1987 | Kamen |
| 4,636,144 A | 1/1987 | Abe et al. |
| 4,682,170 A | 7/1987 | Kubata |
| 4,710,166 A | 12/1987 | Thompson et al. |
| 4,750,643 A | 6/1988 | Wertrich |
| 4,754,786 A | 7/1988 | Roberts |
| 4,783,273 A | 11/1988 | Knutsson et al. |
| 4,798,590 A | 1/1989 | O'Leary et al. |
| 4,835,521 A | 5/1989 | Andrejasich et al. |
| 4,840,620 A | 6/1989 | Kobayashi et al. |
| 4,853,521 A | 8/1989 | Claeys et al. |
| 4,857,056 A | 8/1989 | Talonn |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,925,444 A | 5/1990 | Orkin et al. |
| 4,929,818 A | 5/1990 | Bradbury et al. |
| 4,943,279 A | 7/1990 | Samiotes et al. |
| 4,946,256 A | 8/1990 | Kumble |
| 4,946,439 A | 8/1990 | Eggers |
| 4,950,245 A | 8/1990 | Brown et al. |
| 4,976,687 A * | 12/1990 | Martin ........................ 604/65 |
| 4,978,335 A | 12/1990 | Arthur, III |
| 4,981,467 A | 1/1991 | Bobo, Jr. et al. |
| 5,009,654 A | 4/1991 | Minshall et al. |
| 5,053,002 A | 10/1991 | Barlow |
| 5,059,173 A | 10/1991 | Sacco |
| 5,061,243 A * | 10/1991 | Winchell et al. ............ 604/246 |
| 5,078,683 A | 1/1992 | Sancoff et al. |
| 5,088,981 A | 2/1992 | Howson et al. |
| 5,100,380 A | 3/1992 | Epstein et al. |
| 5,104,374 A * | 4/1992 | Bishko et al. ................ 604/31 |
| 5,128,121 A | 7/1992 | Berg et al. |
| 5,135,000 A | 8/1992 | Akselrod et al. |
| 5,180,896 A | 1/1993 | Gibby et al. |
| 5,199,604 A | 4/1993 | Palmer et al. |
| 5,207,642 A | 5/1993 | Orkin et al. |
| 5,009,654 A | 7/1993 | Minshall et al. |
| 5,230,614 A | 7/1993 | Zanger et al. |
| 5,267,174 A | 11/1993 | Kaufman et al. |
| 5,273,537 A | 12/1993 | Haskvitz et al. |
| 5,274,218 A | 12/1993 | Urata et al. |
| 5,310,997 A | 5/1994 | Roach |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,339,799 A | 8/1994 | Kami et al. |
| 5,349,625 A | 9/1994 | Born et al. |
| 5,354,273 A | 10/1994 | Hagen |
| 5,361,761 A | 11/1994 | Van Lysel et al. |
| 5,362,948 A | 11/1994 | Mormoto |
| 5,368,562 A | 11/1994 | Blomquist et al. |
| 5,378,231 A | 1/1995 | Johnson et al. |
| 5,385,540 A | 1/1995 | Abbott et al. |
| 5,417,213 A | 5/1995 | Prince |
| 5,431,627 A | 7/1995 | Pastrone et al. |
| 5,445,621 A | 8/1995 | Poli et al. |
| 5,450,847 A | 9/1995 | Kampfe et al. |
| 5,458,128 A | 10/1995 | Polanyi et al. |
| 5,460,609 A | 10/1995 | O'Donnell |
| 5,464,391 A | 11/1995 | DeVale |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,496,273 A | 3/1996 | Pastrone et al. |
| 5,507,412 A | 4/1996 | Ebert et al. |
| 5,515,851 A * | 5/1996 | Goldstein ................... 600/431 |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,547,470 A | 8/1996 | Johnson et al. |
| 5,553,619 A | 9/1996 | Prince |
| 5,560,317 A * | 10/1996 | Bunyan et al. ............. 604/246 |
| 5,569,208 A | 10/1996 | Woelpper et al. |
| 5,573,515 A | 11/1996 | Wilson et al. |
| 5,579,767 A | 12/1996 | Prince |
| 5,590,654 A | 1/1997 | Prince |
| 5,616,124 A | 4/1997 | Hague et al. |
| 5,768,405 A | 6/1998 | Makram-Ebeid |
| 5,800,397 A | 9/1998 | Wilson et al. |
| 5,840,026 A | 11/1998 | Uber, III et al. |
| 5,882,343 A | 3/1999 | Wilson et al. |
| 5,916,165 A | 6/1999 | Duchon et al. |
| 5,988,587 A | 11/1999 | Duchon et al. |
| 6,099,502 A | 8/2000 | Duchon et al. |
| 6,385,483 B1 | 5/2002 | Uber, III et al. |

* cited by examiner

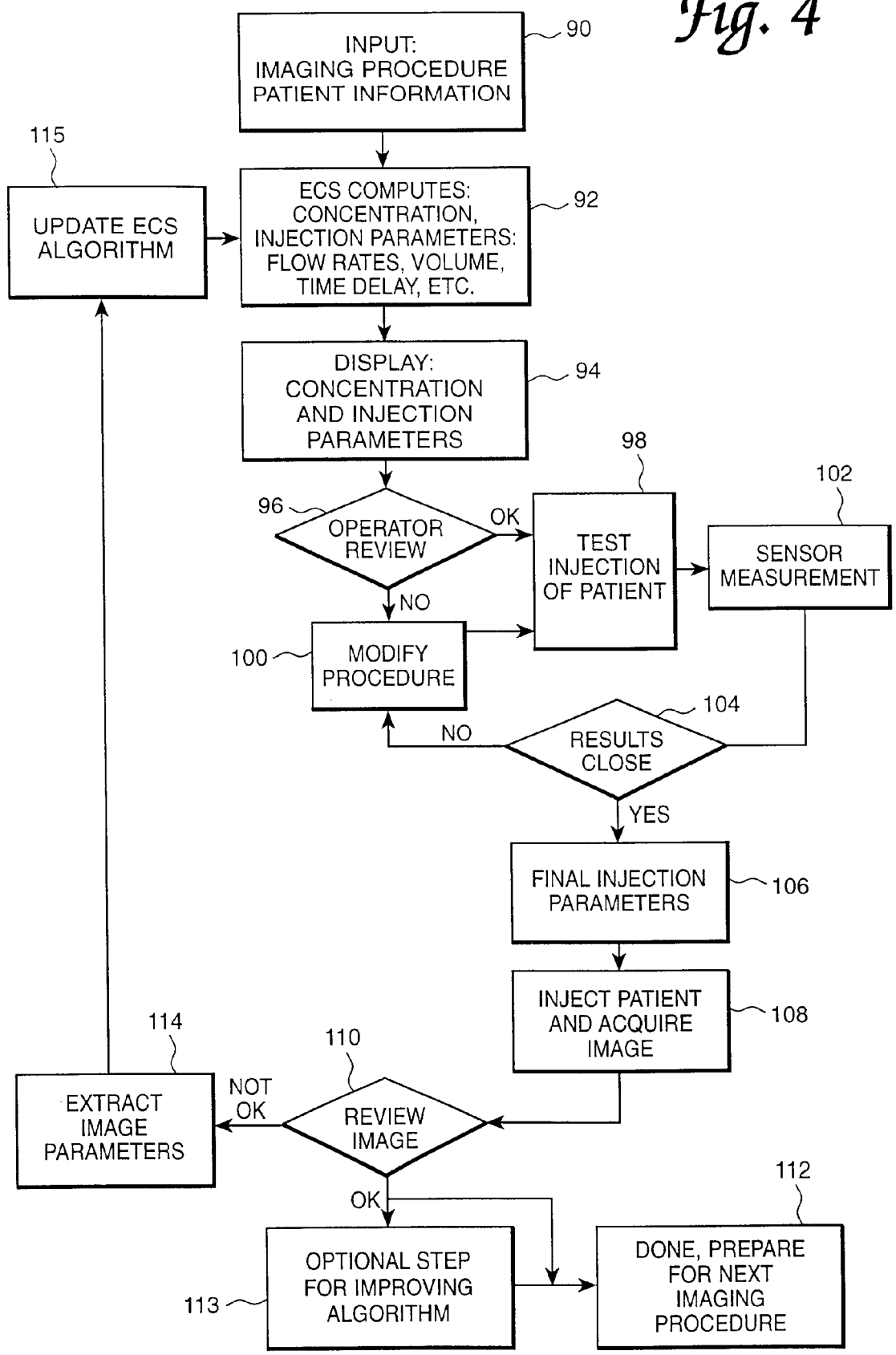

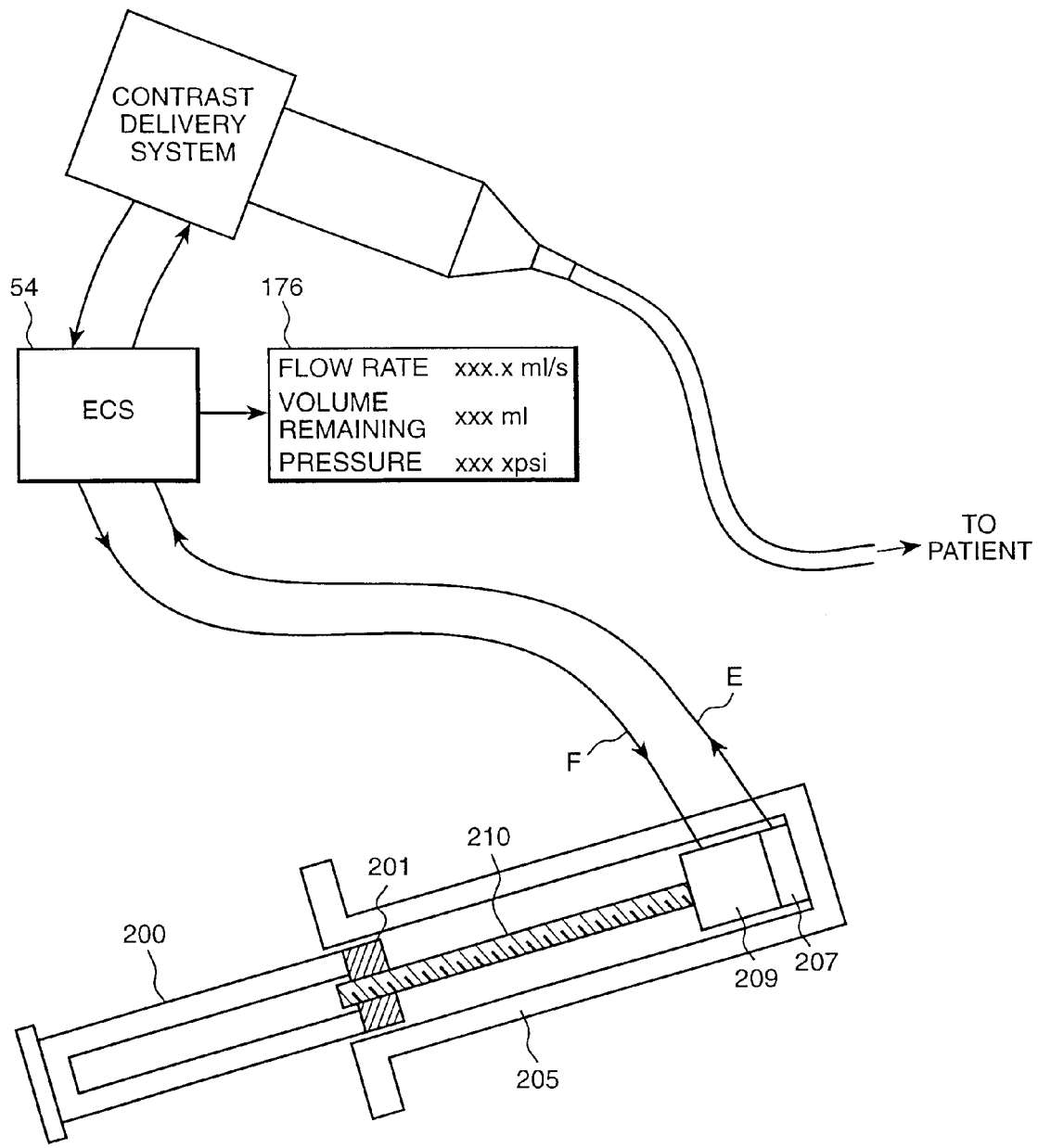

PATIENT SPECIFIC DOSING CONTRAST DELIVERY SYSTEMS AND METHODS

This is a divisional of application Ser. No. 09/197,773, filed Nov. 23, 1998, now U.S. Pat. No. 6,385,483, which is a divisional of application Ser. No. 08/309,820, filed Sep. 21, 1994, now U.S. Pat. No. 5,840,026.

This invention relates generally to the field of medical devices for delivering contrast media during medical diagnostic and therapeutic imaging procedures and more particularly, this invention relates to improved contrast media delivery systems and methods of use which allow adjustment of contrast media concentration and injection parameters either before or during an injection procedure to provide patient specific dosing of contrast media, thus decreasing the waste and cost of these procedures while increasing their efficiency.

DESCRIPTION OF THE RELATED ART

It is well recognized that the appropriate dose for many medications is related to the size and weight of the patient being treated. This is readily apparent in the difference between the recommended doses which most medications have for adults and children. The appropriate dose of contrast media for a given medical imaging procedure is equally dependent upon the size and weight of the patient being examined as well as other additional factors.

Although differences in dosing requirements for medical imaging procedures have been recognized, conventional medical imaging procedures continue to use pre-set doses or standard delivery protocols for injecting contrast media during medical imaging procedures. Using fixed protocols for delivery simplifies the procedure, however, providing the same amount of contrast media to patients weighing between 100 and 200 pounds, for example, produces very different results in image contrast and quality. If the amount of contrast media used is adequate to obtain satisfactory imaging for the 200 pound person, then it is likely that the 100 pound person will receive more contrast media than necessary for the procedure to produce a diagnostic image. With high contrast costs, this is a waste of money as well as increased patient risk.

Standard protocols are used primarily to minimize the potential for errors by hospital personnel and decrease the likelihood of having to repeat the procedure, an occurrence which requires that the patient be exposed to additional radiation and contrast media. Furthermore, in prior art contrast delivery systems, once a bottle of contrast media was opened for use on a patient it could not be used on another patient due to contamination considerations. Existing contrast delivery systems do not prevent the source of contrast media used for an injection from being contaminated with body fluids of the patient. The containers which supplied the contrast media were generally therefore all single use containers and, consequently, the entire container of contrast media was given to the patient being studied.

Present protocols include delivery rate in volume per unit time. Usually the injection is at a constant flow rate or with one change between two fixed flow rates. However, physically, pressure drives fluid flow. Thus, present fluid delivery systems employ some type of servo to develop the pressure needed to deliver the programmed flow rate, up to some pressure limit. The pressure needed depends upon the viscosity of the fluid, the resistance of the fluid path, and the flow rate desired. This is considerably better than the older injector systems which controlled pressure at a set value, and let the flow rate vary.

There are significant drawbacks to fluid delivery systems which are unable to adjust the concentration of contrast media and other injection parameters during an injection procedure. Many patients may receive more contrast media than is necessary to produce an image of diagnostic quality, while others may receive an amount of contrast media insufficient for producing a satisfactory image. Existing procedures also frequently result in waste of contrast media as well as the need for repeating the procedure because an image of diagnostic quality could not be produced.

Some of the shortcomings of existing procedures have been addressed and resolved as described in application Ser. No. 08/144,462, titled "Total System for Contrast Delivery," filed Oct. 28, 1993, now abandoned, and incorporated herein by reference. This application discloses a contrast media delivery system which provides a source of contrast media that is sufficiently isolated from a patient undergoing an imaging procedure that the source of contrast media may be used on additional patients without concern for contamination. Additionally, this system is capable of adjusting contrast media concentration and other injection parameters during an injection procedure.

The system incorporates a source of contrast media and, if desired, a diluent. Each is sufficiently isolated from the patient to prevent contamination. The contrast media preferably has a concentration which is the highest that would be used in an injection procedure so that the operator may combine the contrast media with a diluent and select virtually any concentration of contrast media desired for any given procedure. The concentration of the contrast media injected into a patient may be varied during the injection procedure by varying the ratio of diluent to contrast media. Each patient therefore receives only the amount of contrast media necessary to provide a proper diagnostic image.

It is recognized that this system will be much more versatile and useful if the operator is able to select and adjust contrast media concentration and other injection parameters based on patient information or feedback received during the injection imaging procedures. Additionally, this system would be more efficient if it were capable of automatically choosing the appropriate concentration and injection rate for a given patient. Even more utility and efficiency would be realized from a system that is capable of automatically adjusting concentration and other injection parameters during an injection procedure based on feedback related to the resultant image quality.

Accordingly, it is an object of this invention to provide an improved contrast media delivery system which is capable of automatically varying the injection rate and concentration of contrast media given to a patient during an imaging procedure, based on information received either before or during the injection procedure.

It is another object of the present invention to provide an improved contrast media delivery system which obtains and utilizes feedback information during the imaging procedure to automatically adjust the flow rate, volume and/or concentration of the contrast media into the patient if needed.

It is a further object of this invention to provide a system which is capable of selecting the appropriate injection flow rate and concentration for a given patient based on patient information entered into the system.

Numerous other objects and advantages of the present invention will become apparent from the following summary, drawings, and detailed description of the invention and its preferred embodiment.

SUMMARY OF THE INVENTION

The invention includes apparatus and methods for medical contrast imaging and comprises embodiments which provide patient specific dosing of contrast media in a variety of medical imaging procedures, as opposed to fixed protocols. In this invention, the protocol variables are determined by the system and are dependent upon patient specific information supplied by the operator, and/or information measured by the contrast delivery system either prior to, or during the injection procedure. These apparatus and procedures disclosed herein apply to all of the systems disclosed and described in the application titled "Total System for Contrast Delivery", Ser. No. 08/144,462, now abandoned. Further systems are described in which the system receives input from an operator to provide the appropriate adjustment of system parameters.

In a principal embodiment, information specific to any given patient is entered into the system and the appropriate concentration and injection parameters are computed before initiating the imaging fluid injection procedure. The system is then ready for injection of a patient. It is important to note that the system is not limited to choosing a particular concentration of contrast media or injection rate for the entire procedure, or even a moderate number of phases with constant velocity as present injectors can now do, but rather is capable of selecting an injection profile which may include a continuously varying injection rate and/or concentration of contrast media. The particular injection profile selected by the system is designed to provide the best image quality for the particular patient based on a variety of factors such as patient weight and circulation system variables.

In a refined version of the system, feedback from at least one sensor is employed by the control system to modify the concentration of the contrast media, injection rate, and/or total volume during the injection procedure. Various types of sensors are disclosed for use with this system, in particular, various electromagnetic sensors or video monitoring devices provide feedback for the system or operator to use. In angiography, where the contrast is injected into the region of interest, the sensor needs to make a measurement in that region of interest. In CT and MR it is sufficient for the sensor to measure a remote area of the body, although measuring within the region of interest (ROI) could be advantageous in some applications. The sensor provides an indication of the actual amount of contrast media in the patient. This is used to calculate the appropriate injection rate or concentration of contrast media to provide a diagnostic image with minimum risk and cost.

In critical locations such as coronary arteries, it will take a while for doctors to have confidence in automatically controlled fluid delivery system, thus, rather than automatically altering injection parameters based on feedback signals received from automatic sensors, the concentration, or other injection parameters may be manually adjusted based on images seen by the doctor or operator.

A final version of the invention is disclosed which works to further improve doctors confidence by providing tactile feedback to a doctor or operator in addition to visual or other sensed feedback on the amount of contrast media in a patient. This provides the operator with additional information to use in determining injection rate, concentration and pressure for the injection procedure.

BRIEF DESCRIPTION OF THE DRAWINGS

FIG. 4 is a flow diagram outlining an injection procedure which incorporates a sensor for sensing contrast concentration in a patient during a test injection.

FIG. 10b illustrates an embodiment of the TFC in greater detail.

DETAILED DESCRIPTION OF THE INVENTION AND ITS PREFERRED EMBODIMENT

Figure 1:
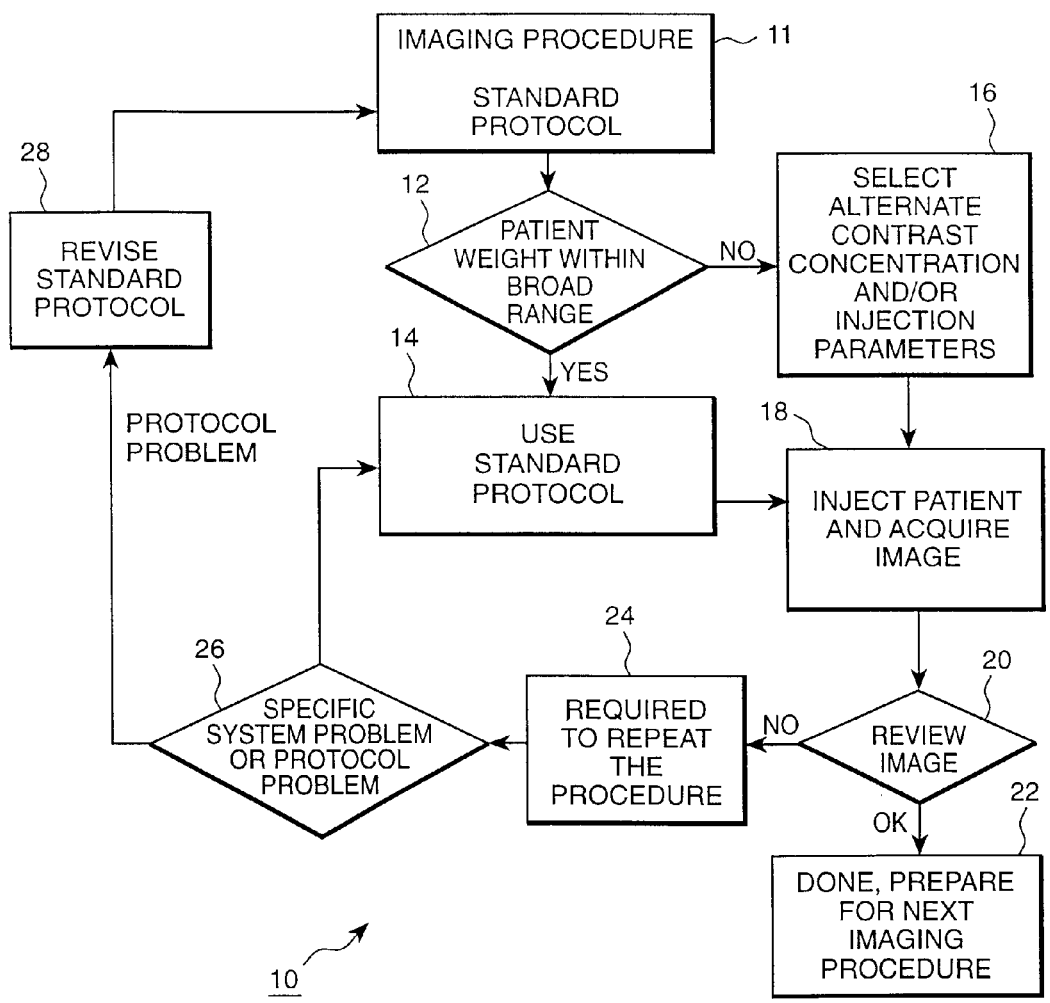
FIG. 1 is a flow diagram illustrating the prior art procedure for implementing a standard protocol.

FIG. 1 is a flow diagram showing a conventional medical imaging procedure for implementation of a standard protocol. This diagram is indicated generally by the numeral 10. The imaging procedure standard protocol is selected at first operative step 11, and a decision is made at step 12 as to whether the patient's weight is within a broad range considered to be appropriate for the particular concentration of contrast media and set of injection parameters for the selected protocol. If the patient's weight is within the broad range of weights acceptable for the particular contrast media and set of injection parameters, the standard protocol is determined to be appropriate at step 14. The patient is injected and the image is acquired at step 18. Alternatively, if the weight of the patient is not within the given range, an alternate contrast media concentration and set of injection parameters are chosen at step 16. Once the alternate concentration or set of injection parameters are chosen at step 16, the patient is then injected and the image is acquired at step 18. The operator then reviews the image at step 20. If the image is satisfactory, the procedure is successfully completed and the system is prepared for the next imaging procedure with this patient or another patient at step 22.

If the image is not satisfactory, the procedure must be repeated as noted at step 24. A decision is then made as to whether there is a specific problem with the system or selected protocol at step 26. If there is a problem with the protocol, the selected protocol is revised at step 28. Alternatively, if the initially selected protocol is appropriate, step 14 is repeated and the patient is injected at step 18. As noted, this type of system and its lack of versatility has significant disadvantages compared with the system of the present invention.

The present invention takes advantage of the increased versatility of the advances set forth in the co-pending application previously noted and further advances the art by adding automatic functions and increased versatility.

Figure 2:
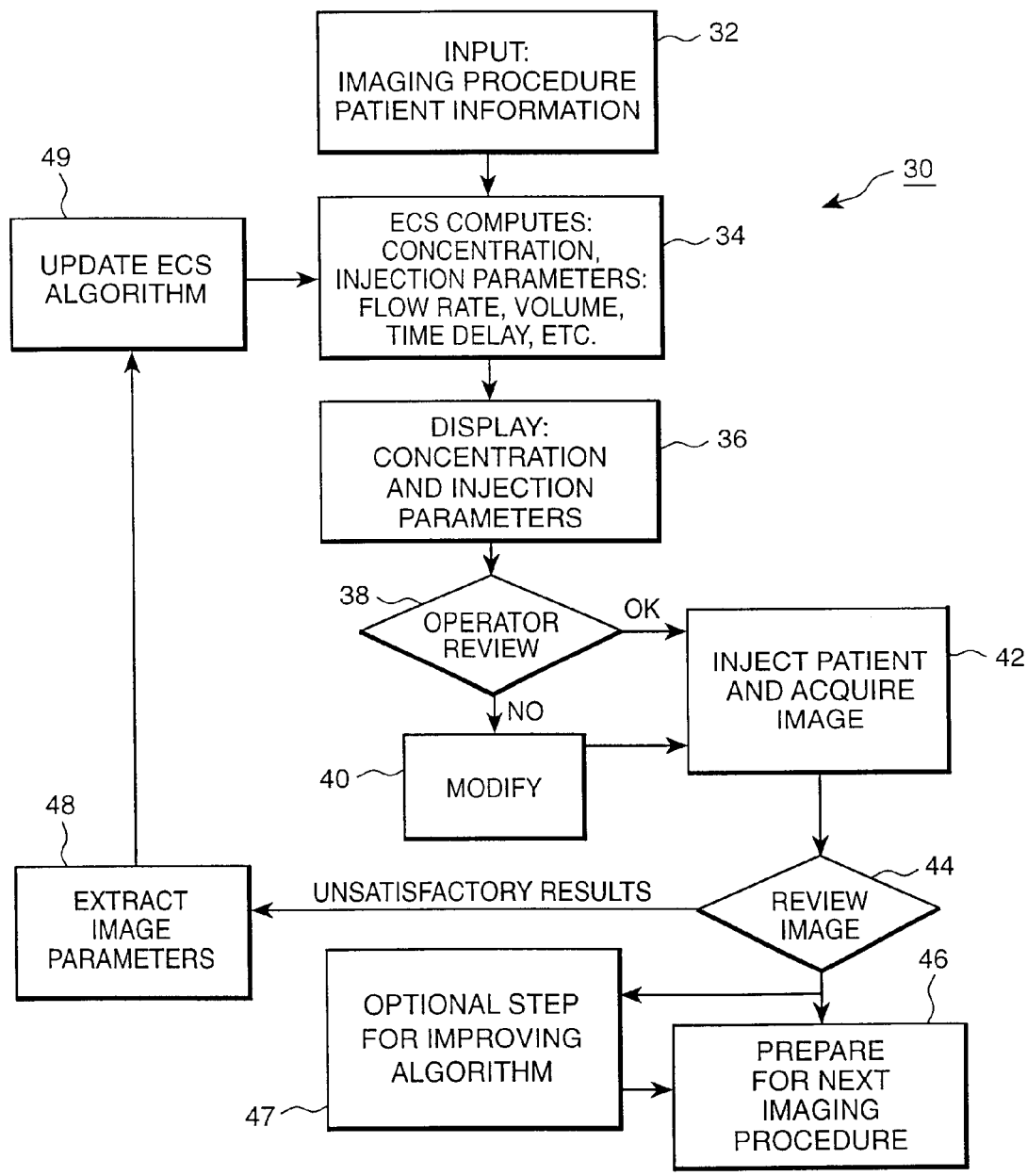
FIG. 2 is a flow diagram for a system of the present invention in which injection parameters are calculated based on patient specific information.

A flow-diagram illustrating an improved contrast media delivery of the present invention is shown generally by the numeral 30 in FIG. 2. In this system the operator initially inputs information relating to the patient such as size and weight in addition to other factors related to the particular imaging procedure being performed at first operative step 32. This information could be stored in a hospital computer and simply downloaded to the imaging system. The Electronic Control System (ECS) of the contrast media delivery system then determines the appropriate concentration of the contrast media and other injection parameters such as flow rates, volume, time delay, etc. at step 34. The computed concentration of contrast media and injection parameters are then displayed at step 36.

In this and other embodiments, the step of displaying parameters for user review is optional. As this capability is first introduced, operators will want to retain control. As they become familiar with the equipment and gain confidence with it, it will be possible to manufacture and market systems which no longer display injection parameters for operator review. In the preferred embodiment, however, the system operator then reviews the calculated parameters at step 38 and decides whether to manually modify the parameters at step 40 or proceed with the injection of the patient at step 42. The injection begins in step 42, the image is acquired, and the system operator or physician reviews the resulting image at step 44. If the image is satisfactory for diagnosis, the image is stored and the procedure is complete. The system may be prepared for the next imaging procedure at step 46. Prior to preparing the system for the next imaging procedure, the operator may choose to perform optional step 47 in which the operator may input information to modify the algorithm which determines the injection parameters so that before the system stores the parameters they are set to levels which would have provided an image which is more personally satisfactory. The system software keeps track of the various injection parameters a doctor or operator selects for patients of a particular size and for a given procedure. These factors are analyzed for preferred tendencies of the doctor or operator so that the system is able to select injection parameters based on the operators personal preferences. By performing this optional step, the system will be able to automatically select operating parameters which provide a more satisfactory image for an individual. If the operator chooses to perform optional step 47, the system is prepared for the next imaging procedure upon completion of this step.

Alternatively, if the image is not satisfactory, the image parameters are extracted at step 48 and the ECS is updated at step 49. The ECS then recalculates new parameters and repeats step 34. The remainder of the procedure is also repeated. It is anticipated that this will happen very seldom once the algorithm is adapted to the doctor's preference.

Figure 3A:
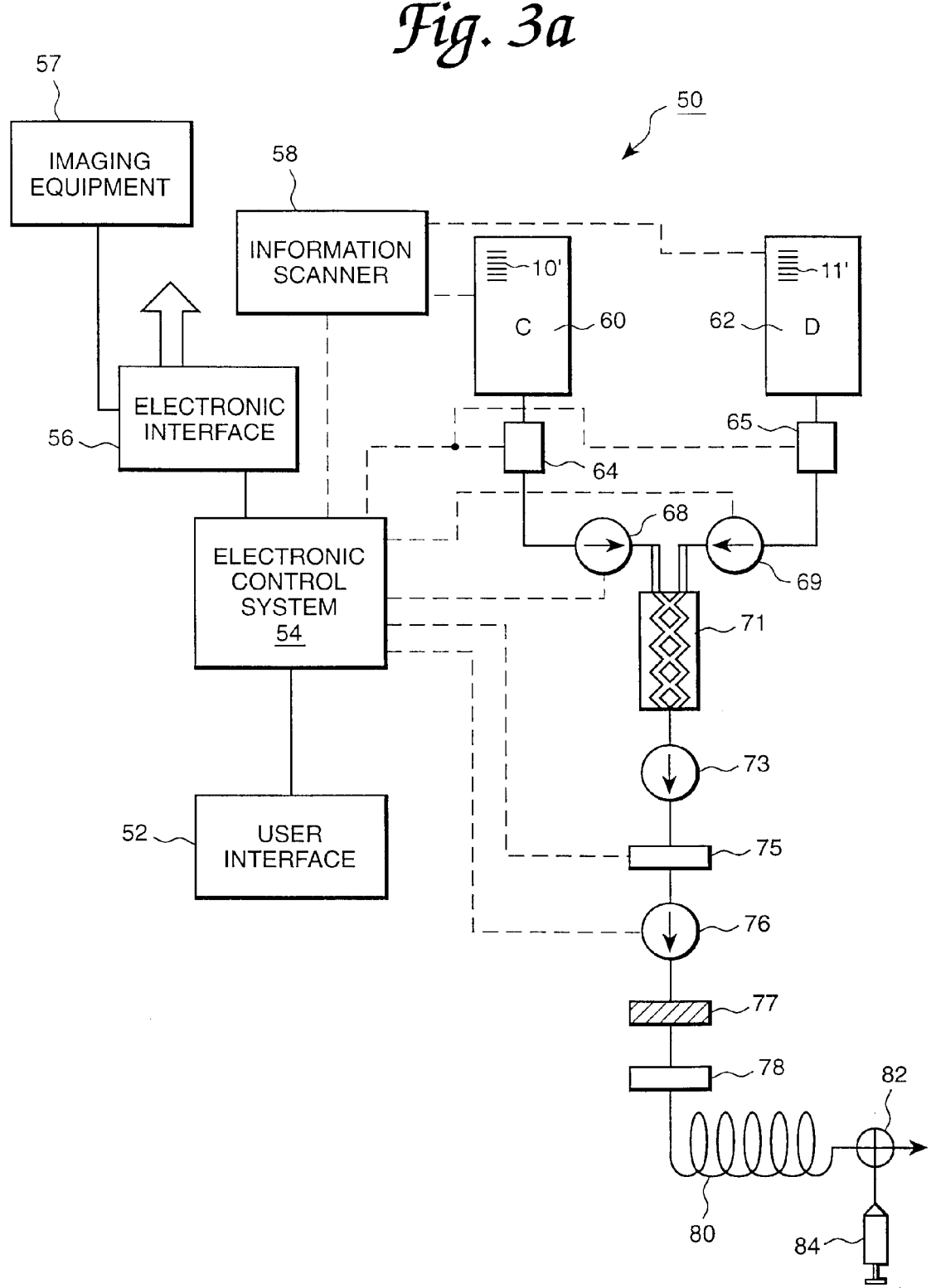
FIG. 3a illustrates an embodiment of the present invention which employs the improved procedure for calculating injection parameters of the present invention.

FIG. 3a illustrates an embodiment of the improved contrast media delivery system of the present invention generally at 50. The user interface of the ECS is indicated at 52 with direct connection to the ECS 54. There is an additional electronic interface 56. The electronic interface 56 may be connected to other systems which are not shown, such as imaging equipment and the hospital information system. If this interface is connected to the hospital information system, it could rely on this system to receive patient specific information necessary for performing the procedure such as size, weight, etc. An operator would therefore only be required to input a patient number and the appropriate information would be downloaded from the hospital information system.

The electronic interface 56 is also connected to the imaging equipment 57. The ECS is capable of sending and receiving information so that, for example, the operator only needs to program the CT scanner with the number of slices and section of the body being imaged. This would be transmitted to the contrast delivery system to be used in determining flow rates and delays, etc. Additionally, information relating to image quality or sensed concentration of contrast media is received to allow for automatic adjustment of the system.

An information scanner 58 is also shown with direct connection to the ECS 54. The information scanner 58 scans information encoded and attached to fluid storage tanks for the contrast container 60 and diluent container 62. The information encoded and read by the scanner 58 includes information such as tank volume, type and concentration of fluid etc. This information is then employed by the ECS in controlling and calculating the implementation of the imaging procedure. Alternatively, this information is downloaded from memory located on a fluid delivery module as noted in the application titled Closed Loop Information Path for Medical Fluid Delivery Systems, application Ser. No. 08/273,665, filed Jul. 12, 1994, now abandoned.

Contrast and diluent tank volume, type and concentration of fluid is stored in the system memory and is updated after using the system. The system is therefore able to automatically warn the operator when the system is running low on contrast or diluent. Additionally, the system is able to warn the operator if the wrong contrast media was connected for a particular procedure.

The ECS 54 is also connected to respective contrast and diluent heaters 64, 65. The ECS 54 controls the heaters 64, 65 through this connection and receives feedback so that the system may make appropriate adjustment of the heaters to provide the desired temperature of contrast media. Metering pumps 68, 69 are connected to the ECS 54 which also controls fluid flow of contrast and diluent through the pumps.

The output of each of the metering pumps 68, 69 is connected to the helical vane static mixer 71 which ensures that the desired concentration of contrast media is produced by the system. A backflow valve 73 in the fluid flow path to the patient prevents the contrast media from returning to the sources of contrast and diluent 60, 62 and causing contamination. A fluid assurance sensor 75 is also directly connected to the ECS 54. The final element in the fluid path which is connected to the ECS 54 is the pressurizing pump 76. The pressurizing pump 76 provides the desired injection rate of contrast media for the particular procedure. A per patient connector 77 is followed by a sterile filter 78 which is also connected in line to prevent contamination of the sources of contrast media and diluent by preventing body fluids of the patient from flowing back into the sources of contrast and diluent. The fluid path then flows through connector tube 80 and a medical stopcock 82.

A hand held syringe 84 is also connected to a port of the stopcock 82 to allow the doctor to perform what are considered test or scout injections. For example, the doctor may get a small amount of fluid at a concentration, and then do hand powered injections during his manipulations to get a catheter into the proper vessel. In a preferred embodiment, a contrast media sensor (not shown) is added to the system to provide additional feedback during an injection procedure in order to provide for better monitoring of concentration as it is adjusted by the system.

Figure 3B:
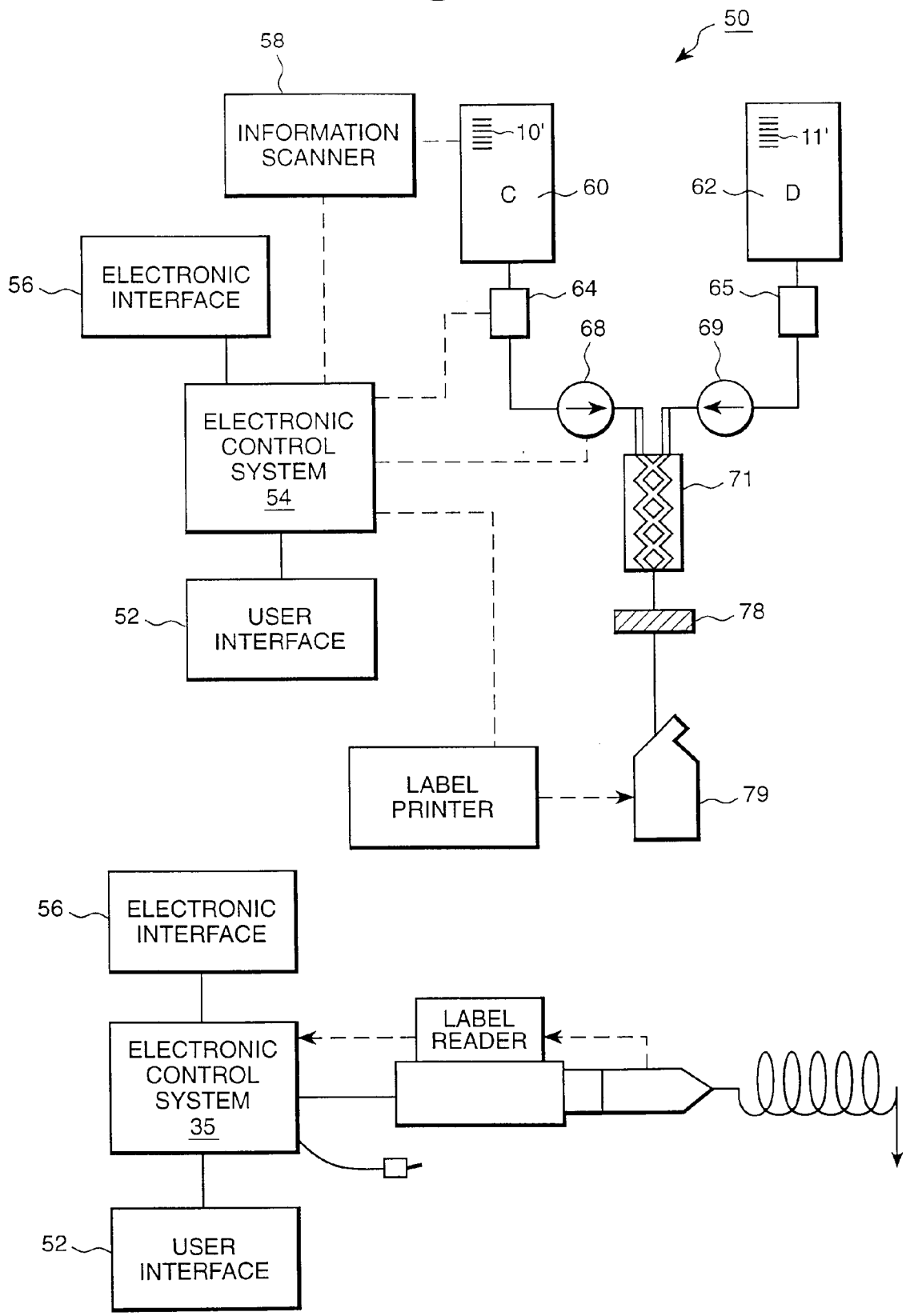
FIG. 3b illustrates an embodiment of the present invention which employs the improved procedure for calculating the filling of a syringe used with an injector.

FIG. 3b illustrates a second embodiment of the improved contrast media delivery system of the present invention generally at 50. Most of the system components and their function are identical to those of FIG. 3a, but instead of the per patient connector 77, sterile filter 78, tubing 80, connector 82 and hand syringe 84, 3b has a syringe 79 which is filled with fluid. This syringe is then placed in an injector for delivery of the fluid to the patient. Prevention of contamination is accomplished by having the syringe allowed to be filled only once. The label printer prints the patient specific injection information, and this label is then read by the ECS of the injector. The injector ECS 35 can utilize any of the improved patient specific processes of this invention, such as sensors or tactile feedback controllers, neither of which are shown.

Alternatively, the injector ECS 35 could communicate with the filling station ECS 54 so that the injector is programmed by the filling station. A third alternative involves having the filling station user interface 52 display the injector parameters and then the operator enters these parameters into injector ECS 35 via the injector user interface. An advantage of this most manual system is that it can work with present injector equipment, enabling the customer to achieve patient specific dosing while utilizing equipment which he has already purchased.

One embodiment, not shown, that uses even less hardware and sophistication consists of only a user interface and an electronic control system. The operator enters the patient specific data, and the volume, concentration and injection parameters are displayed for the operator. Then the operator manually fills the syringe using a manual method, such as that supplied by NAMIC, of Glens Falls, N.Y., preserving any unused contrast for the next patient. The injector is then automatically or manually programmed according to the patient specific parameters computed, and is ready to inject.

It will be appreciated that various devices could be employed to function as the ECS 54. ECS 54 at the very least must incorporate a microprocessor and memory along with control outputs for the various devices. It is understood that software controls the system. The software relies on a variety of factors for calculating the appropriate contrast media concentration and injection parameters for a particular patient.

The appropriate weight given to each of the factors in the software for calculating these parameters cannot now be disclosed because of the varied relationship between these factors and the numerous imaging systems and sensors which may use this invention. It is contemplated that experimentation with various weight factors applied to the variables will provide the best results with any given system. This is why embodiments are described with varying degrees of operator control, operator verification and automatic operation.

The following table provides an outline of the factors which the system may consider in evaluating the appropriate concentration of contrast media and injection rate for a particular patient as well as the general effect an increase in these factors would have on calculation of the injection parameters. Some factors such as weight have a continuous effect. A slightly heavier patient gets a little more contrast. Others, such as hydration or kidney function have no effect until some threshold is crossed.

TABLE I

| INPUT PARAMETER | EFFECTED PARAMETER | EFFECT |
|---|---|---|
| FOR INTRA VENOUS | | |
| Patient Weight | Total volume (mg of Iodine) | Increases |
|  | Flow rate to get mgI/kg/sec | Increases |
|  | Concentration (optional) | Increases |
| Patient Hydration | Concentration | Increases |
| Kidney Function | Use minimum total mgI if poor or questionable |  |
| Cardiac Status | With poor status, use minimum total fluid volume to minimize fluid loading |  |
| Circulation Transit Time | Use longer delay time until start of scanner if circulation time is poor Change from single phase to multi-phase or continuously varying |  |
| Length of Scanning | Flow rate | Decreases to lengthen image contrast time |
| Connector tube diameter or catheter size | Provides limit to prevent over pressure |  |
| Patient vein status | If weak, use lower concentration, lower flow rate |  |
| FOR INTRA ARTERIAL | | |
| Vessel Diameter | Flow rate | Increases |
|  | Volume of Injection | Increases |
|  | Concentration | Increases |
| Catheter Diameter | Concentration | Increases |
| Procedure/body location | Duration of injection | Varies |
| Patient Weight | Limit on total iodine dose | Increases |

Given the variety of factors to be considered, fuzzy logic or neural networks may be appropriate for implementation of the program, however, a conventional computer program also provides satisfactory results.

FIG. 4 illustrates a flow-chart of the injection procedure of the present invention with sensor measurement. In this procedure, a test injection is made and a contrast media sensor is used to provide feedback on the actual concentration of contrast media within the patient. Initially, the operator enters the type of imaging procedure to be performed and patient information at first operative step 90. It is important to note the system will already be aware of the type and concentration of the fluid available in the system tanks because the information scanner would have input this information when the tanks were installed. In the next step 92, the ECS computes the appropriate concentration of contrast media and the injection parameters such as flow rates, volume, and time delay etc. The resultant concentration and injection parameters are then displayed at step 94. The operator then reviews the parameters and decides whether to manually modify the procedure at step 96.

If the operator is satisfied with the injection parameters, a test injection of the patient is performed in step 98. Alternatively, the operator may modify the procedure in step 100 and then perform a test injection of the patient at step 98. A sensor measurement of the concentration of contrast media within the patient's body is then performed at step 102 and a decision is made at step 104 as to whether the results of the sample injection are sufficiently close to the desired value. If the results of the test injection are not satisfactory, the system returns to step 100 to modify the injection parameters, either manually or automatically and then repeats the test injection at step 98.

When the results of the test injection are satisfactory, the final injection parameters are selected at step 106 which may involve having the operator fine tune the procedure by making minor adjustments and updating specific parameters to provide more desirable results. If more significant changes are needed, the test injection should be repeated as noted. The imaging injection procedure begins at step 108. Upon completion of the injection procedure step 108, the operator reviews the image at step 110 and determines whether the procedure produced a satisfactory diagnostic image. If the image is satisfactory, the procedure is complete and the system may be prepared for the next imaging procedure at step 112. Step 113 is an optional step which may be performed before preparing the system for the next imaging procedure if the operator wishes to update the algorithm which determines the injection parameters that are used to customize injection procedure to a doctor's preference.

Alternatively, if the image is unsatisfactory, the image parameters are extracted at step 114 and the ECS injection parameters are updated at step 115. The procedure is repeated beginning with recalculation of the injection parameters step 92. It is anticipated that this will happen very seldom once the algorithm has been adapted to the imaging equipment and the doctor's preferences as previously noted.

Figure 5:
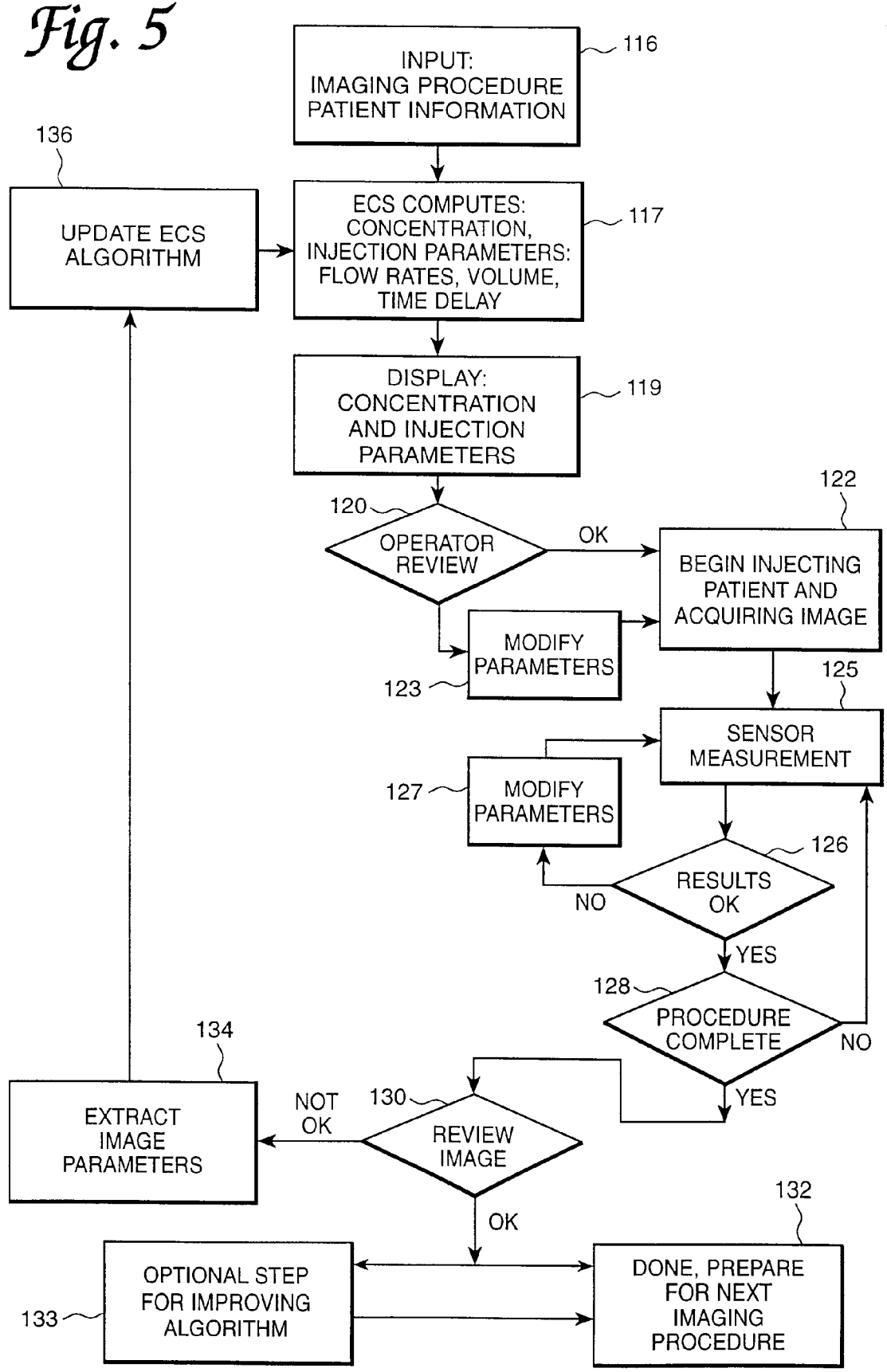
FIG. 5 is a flow diagram outlining an injection procedure which incorporates a sensor for sensing contrast concentration in a patient for modifying the injection parameters throughout the injection.

FIG. 5 illustrates an alternate procedure for performing an imaging procedure with the improved contrast delivery system of the present invention. In this procedure, a sensor measurement is used throughout the injection procedure to provide an indication of the actual concentration of contrast media within the patient. Initially, information relating to the particular imaging procedure to be performed and patient are input to the system at step first operative step 116. The ECS computes concentration, and other injection parameters such as flow rates, volume, time delay, etc. at step 117. The calculated concentration of contrast media and other injection parameters are then displayed at step 119 and the operator reviews the calculated results and determines whether they are satisfactory at step 120. If the results appear to be within the desired range, injection of the contrast media begins in step 122.

Alternatively, the operator may modify the injection parameters at step 123 before initiating the injection at step 122. A sensor measurement is made at step 125 and a decision is made as to whether the results are satisfactory at step 126. If they are not satisfactory, the injection parameters are modified at step 127 and the sensor measurement is continued at step 125. The sensor measurement is made and the injection parameters are adjusted throughout the injection process based on the sensor measurements. The adjustments continue until the procedure is complete as indicated at step 128. If the sensor measurement indicates a serious problem, the system may automatically stop the injection procedure depending on the severity of the problem. Upon completion, the operator then reviews the image at step 130 and decides whether the results are satisfactory.

If satisfactory results are achieved, the system is prepared for the next imaging procedure as indicated at step 132. Step 133 is an optional step which may be performed before preparing the system for the next imaging procedure if the operator wishes to update the algorithm which determines the injection parameters to customize the injection procedure to a doctor's preference.

Alternatively, if the results are not satisfactory, the image parameters are extracted at step 134 and the ECS injection parameters are updated at step 136. The ECS then recalculates the concentration of contrast media and injection parameters at step 117 and the operator repeats remaining steps in the procedure. Again, this will be a seldom occurrence once the doctor's preferences have been included. In this embodiment and all others, the repeat procedure may need to be postponed if the patient is near the maximum daily contrast dose.

Having the sensor provide to the ECS, a measure of contrast in the body during an injection and having the ECS be able to continuously adjust fluid concentration, flow rate, and/or timing of the signals to start the imaging equipment provides an ability to optimally adapt the dosing to patient specific parameters which may be unknown or inaccurately estimated before the start of the injection. For example, in a CT injection, contrast may arrive at a site more quickly in some patients than others.

Systems are available which allow the operator to adjust the timing of the beginning of CT scans, however, these systems, unlike the systems of the present invention, are unable to adjust the flow rate, concentration, and/or stop the injection sooner than originally planned, thus limiting the amount of contrast injected into the patient, saving money and reducing patient risk.

Figure 6:
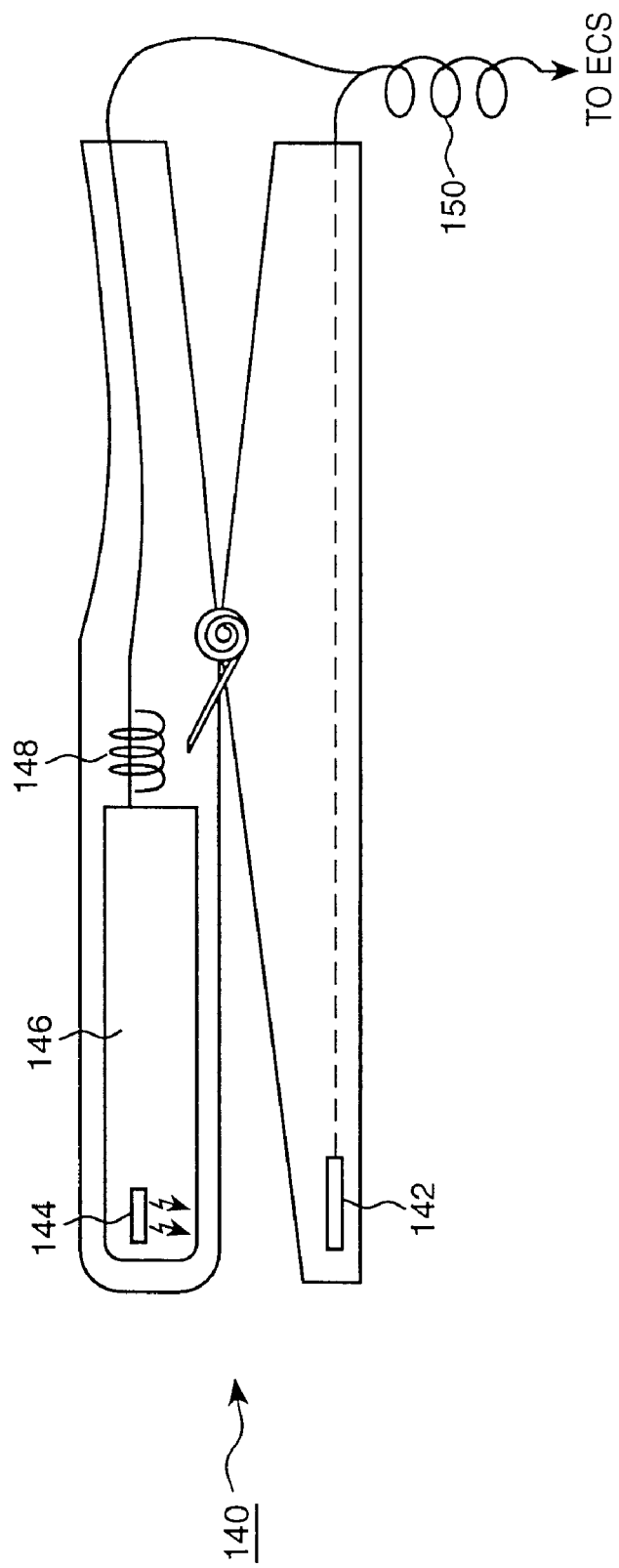
FIG. 6 illustrates an example of a sensor for use with the present invention.

FIG. 6 illustrates an example of a sensor which can be used with the improved contrast media injection system of the present invention. The sensor is shown generally at 140. It is contemplated that a variety of sensors may be used for evaluating the concentration of contrast media within a patient at particular time. These sensors use various wavelengths of electromagnetic radiation to determine the presence of contrast media. The particular sensor disclosed in FIG. 6 is designed for sensing contrast media used during procedures which use x-rays to create the desired image. Therefore this sensor employs a source of x-rays and a receiver for determining the amount of x-ray radiation which passes through the tissue of a patient. It is understood that use of other sensors for x-ray or different types of contrast media could be used in a similar manner.

The sensor includes a silicon diode radiation detector 142 and source of radioactive material 144. A moveable shield 146 is capable of alternately shielding and exposing the radioactive material 144 to the radiation detector 142. Electronic actuator 148 moves the shield 146 upon command from the ECS. The sensor includes control and power cables 150 connected to the ECS not shown. It has been found that a small radioactive source works best. One example of a commercially available product which can be used to generate an output which varies depending upon the level of x-rays passing through body tissue is the Lixi scope manufactured by Lixi, Inc. of Downers Grove, Ill. 60515. This product uses a similar design for portable imaging of small body parts such as the hand or ankle. Although this product is designed for producing images, it is also capable of being adapted to provide signals which are proportional to the level of contrast media in a patient. When used with the system of the present invention, the source and detector are placed on opposite sides of a thin tissue region such as the ear lobe, finger tip, or fleshy part of the hand between the thumb and index finger. It is known that the attenuation of the tissue will change as the concentration of x-ray contrast builds up in the blood and then surrounding tissue. It should be noted that the radioactive source should be shielded when not in use.

Another type of sensor which could be used with the system is one which employs visible or infrared (IR) light, preferably of two different wavelengths. This is similar to the technique currently employed in pulse oximeters. It is known that iodinated contrast interferes with the signals used to make oxygen measurements with pulse oximeters and that these systems are capable of measuring the level of iodinated contrast. Most x-ray contrasts contain a benzene ring with three iodine atoms attached at positions 1, 3 and 5. Various organic molecules are attached at positions 2, 4 and 6. The infrared spectrum for iodine atoms bonded to a benzene ring is unlike those for naturally occurring compounds. Dual or multiple wavelengths help to minimize interference or prevent positioning differences from giving incorrect readings. Sensors with other visible, IR or different electromagnetic wavelengths would be used for MRI or ultrasound contrast materials.

Another sensor which could be used with the improved injection system of the present invention is a pressure sensor inserted into a vessel. A tiny pressure sensor on an IC, such as those made by SenSim, Inc., Sunnyvale, Calif., are capable of providing this type of feedback. A dual lumen catheter and a conventional blood pressure monitor could be also used. During the injection procedure, the flow rate of the injector would be adjusted based upon the sensed intra-luminal pressure. For intravenous injections, the pressure within the vein could be used to limit or appropriately adjust flow rate or concentration to prevent vessel damage or extravasation. For intra-arterial injections, appropriate adjustment would minimize backflow by timing variations in flow rate to match internal variations due to pressure waves created by the heart. When backflow occurs, some of the injected contrast moves upstream in the vessel and may go to unintended side vessels. This is not usually dangerous, but does represent a waste of contrast. Measuring the pressure at one or more places in the artery or vein during injection provides the information which is necessary to safely inject the optimum amount of contrast.

Regardless of the type of sensor used by the system, it is contemplated that the sensor will send a feedback signal to the ECS such as a voltage proportional to the concentration of contrast media present in a patient. The system could then either provide this information to the system operator for manual adjustment of the injection parameters, or alternatively, the system could use these signals to automatically adjust the concentration of the contrast media or the flow rate to provide a more desirable image. For intra-arterial, the delay between change in injection parameter and effect is small enough so that the operator may be part of the feedback loop. For intravenous injections, the delay is longer and variable, so having the ECS measure and automatically account for the delay is preferable.

Figure 7:
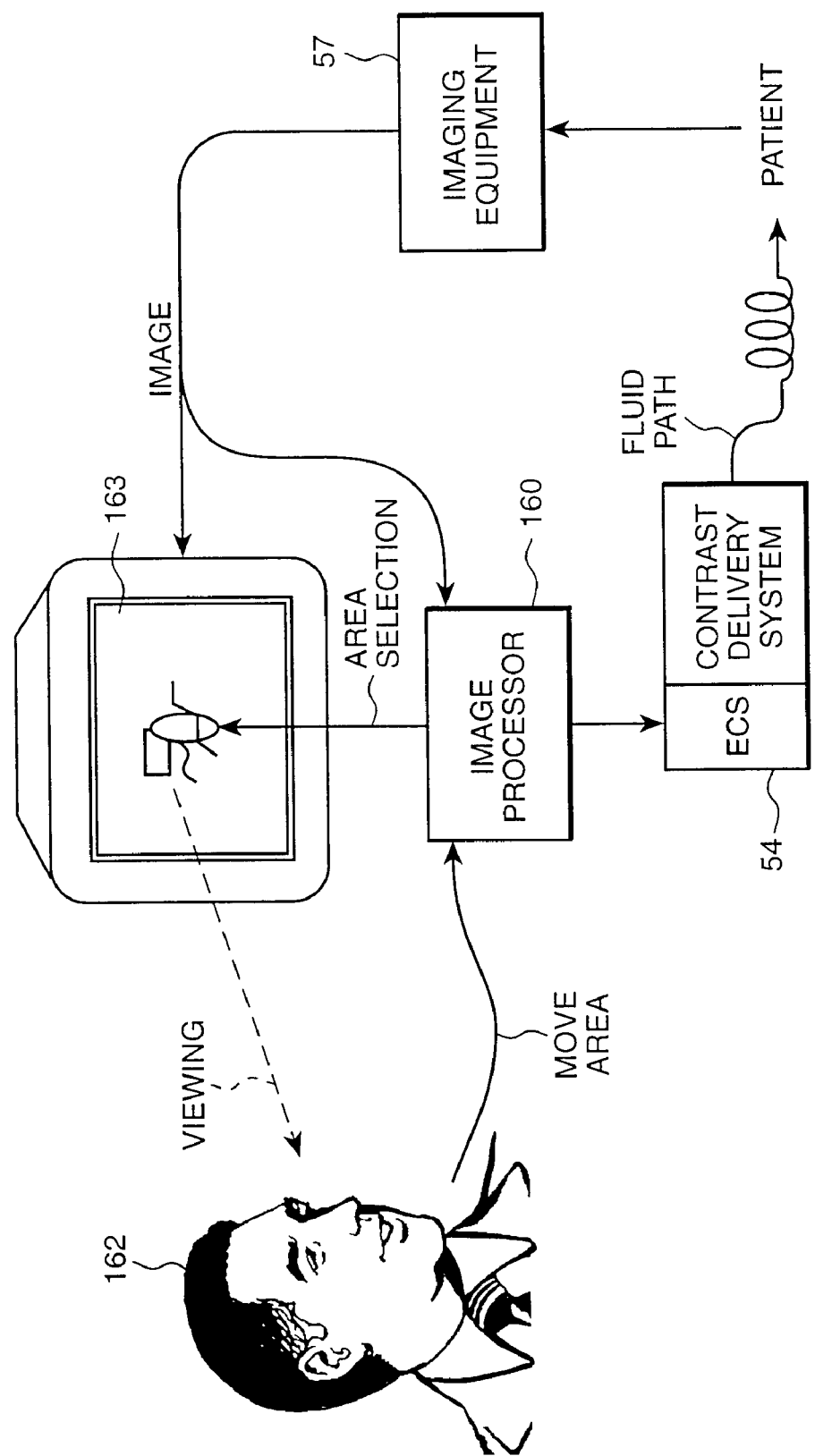
FIG. 7 illustrates the present invention wherein the system is able to automatically adjust fluid flow rate based on the resulting image.

FIG. 7 illustrates another embodiment of the present invention. In this embodiment, the system is capable of automatically adjusting the injection parameters to alter the image produced by the system based upon feedback from the actual image. This embodiment includes an image processor 160 which analyzes a bitmap of the video image produced by the contrast delivery system in conjunction with the imaging equipment 57. The operator 162 selects one area of interest on the image via the monitor 163, for example, by moving a box or pointer over the area via a user interface such as a mouse and then selecting the position by clicking the mouse. The user selects a desired area of interest such as a blood vessel being examined. The image processor 160 then calculates the average intensity of the pixels in the designated area. It is understood that pixel intensity would be proportional to the amount of contrast media in the patient's body due to the effect on the electromagnetic wave or ultrasonic energy wave being used for the imaging procedure. Depending upon the resultant average pixel intensity, the system then makes appropriate adjustments in contrast concentration and injection rate.

The use of a video image for providing feedback to make adjustments to the injection parameters requires real time or approximately real time display of the ROI. All x-ray fluoroscopic systems provide real-time video. One such system that is capable of providing such images in CT is a system called Smart Prep manufactured by General Electric of Milwaukee, Wis. Once the injection is started with this system, a scan is repeated periodically after a small delay. A delay of approximately eight seconds is of short enough duration to provide satisfactory results. The concentration of the contrast in the ROI's is measured on each scan and plotted for the operator. In the General Electric system, this plot is used to help the operator decide when to begin scanning the organ. In the invention described herein, a mechanism similar to GE's may also be used as the sensor input to the ECS to automatically control the flow rate or concentrations.

Another way in which the system of the present invention can use the resulting image for adjusting the injection parameters is for the operator to select two areas of interest on the image. The system produces a relative pixel intensity measurement by calculating the difference in pixel intensity between the two different areas. The operator selects one area located in the background and second area located within part of the patient being examined such as a blood vessel of interest. The image processor calculates the appropriate concentration of contrast media based upon the resulting measurement.

Figure 8:
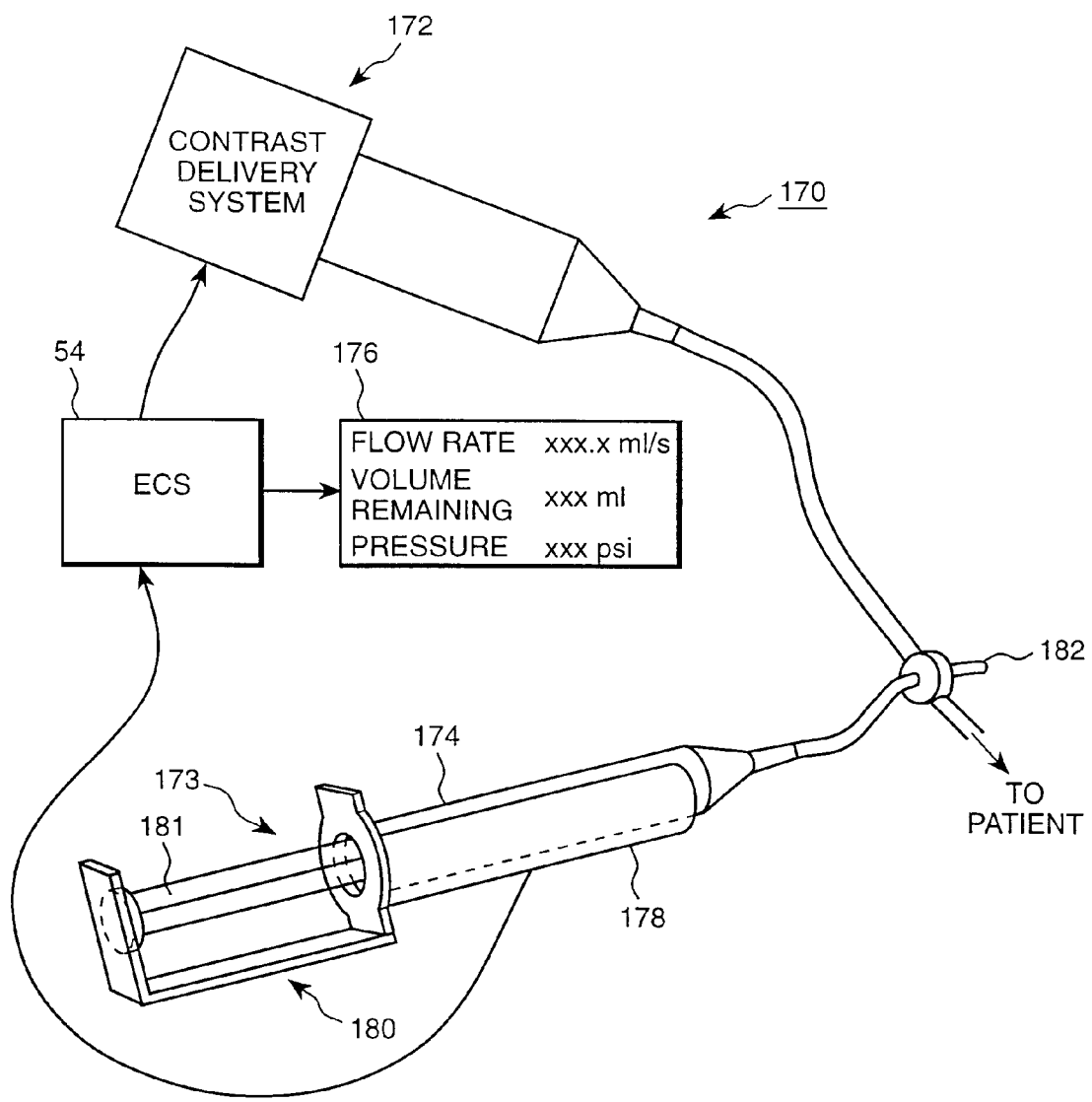
FIG. 8 illustrates an embodiment of a tactile feedback pressure measurement device which allows the system operator to adjust injection parameters based on tactile feedback.

A further embodiment of the present invention is disclosed in FIG. 8. The injection system is shown generally at 170. The ECS 54 is connected to the contrast delivery system 172 and an embodiment of a Tactile Feedback Control (TFC) unit 173. An additional connection is made between the ECS and the user display 176. The TFC 173 comprises a disposable syringe 174 which is located within a durable/reusable cradle 178. The cradle 178 is electrically connected to the ECS 54 and is physically connected to a sliding potentiometer 180 which is driven by plunger 181.

The doctor holds the cradle and syringe during the injection procedure and as the doctor depresses the sliding potentiometer/syringe piston assembly, the plunger is moved forward, displacing fluid toward the patient and creating a pressure in the syringe. The sliding potentiometer 180 tracks the position of the syringe plunger. Alternatively, optical encoders could be used to prevent contact skipping thus increasing the system reliability.

The ECS controls the Contrast Delivery System (CDS) to inject an amount of fluid into the patient based on the change in position of the plunger. The disposable syringe 174 is in fluid communication with a multi-port stopcock 182. As the fluid is injected, the pressure the doctor feels in his hand is proportional to the actual pressure produced by the contrast delivery system. The force required to move the piston provides the operator with tactile feedback on the pressure in the system. The doctor is able to use this feedback to ensure the safety of the injection procedure. Separate from this mechanism, the ECS may employ other pressure measurement mechanisms such as the contrast delivery system motor drive current.

The primary benefit over a totally manual injection is that the doctor is not required to develop the pressure and flow rate. He only develops the pressure and pushes some of the fluid. The required manual power output (pressure*flow rate) is decreased.

The ECS also incorporates preprogrammed flow rate and pressure limits which prevent the pressure of the injection from exceeding safe limits. Additionally, the user display 176 incorporates warning lights which indicate when certain pressure levels have been exceeded as well as an indication of the actual pressure.

The ECS of the preferred embodiment of the present invention also stores the injection parameters or flow rate profiles used by individual doctors or other system operators so that the system is able to customize injection procedures to match the particular injection profile preferred by the individual. It has been recognized that doctors have varying preferences in the images used for diagnosing patients during medical imaging procedures. Varying degrees of contrast media concentration and injection rates alter the contrast in the resultant image. The system would be able to use information on a doctor's preference to customize procedures primarily based on the type of procedure and the weight of the patient. These and other injection statistics would be stored and after a sufficient sample size was available in system memory for the particular doctor or system operator, the system would make minor adjustments to the weight given to variables in the injection parameter calculation algorithm used by the ECS. This would enable the system to operate in the more automatic modes illustrated in FIGS. 2, 4, or 5.

Figure 9:
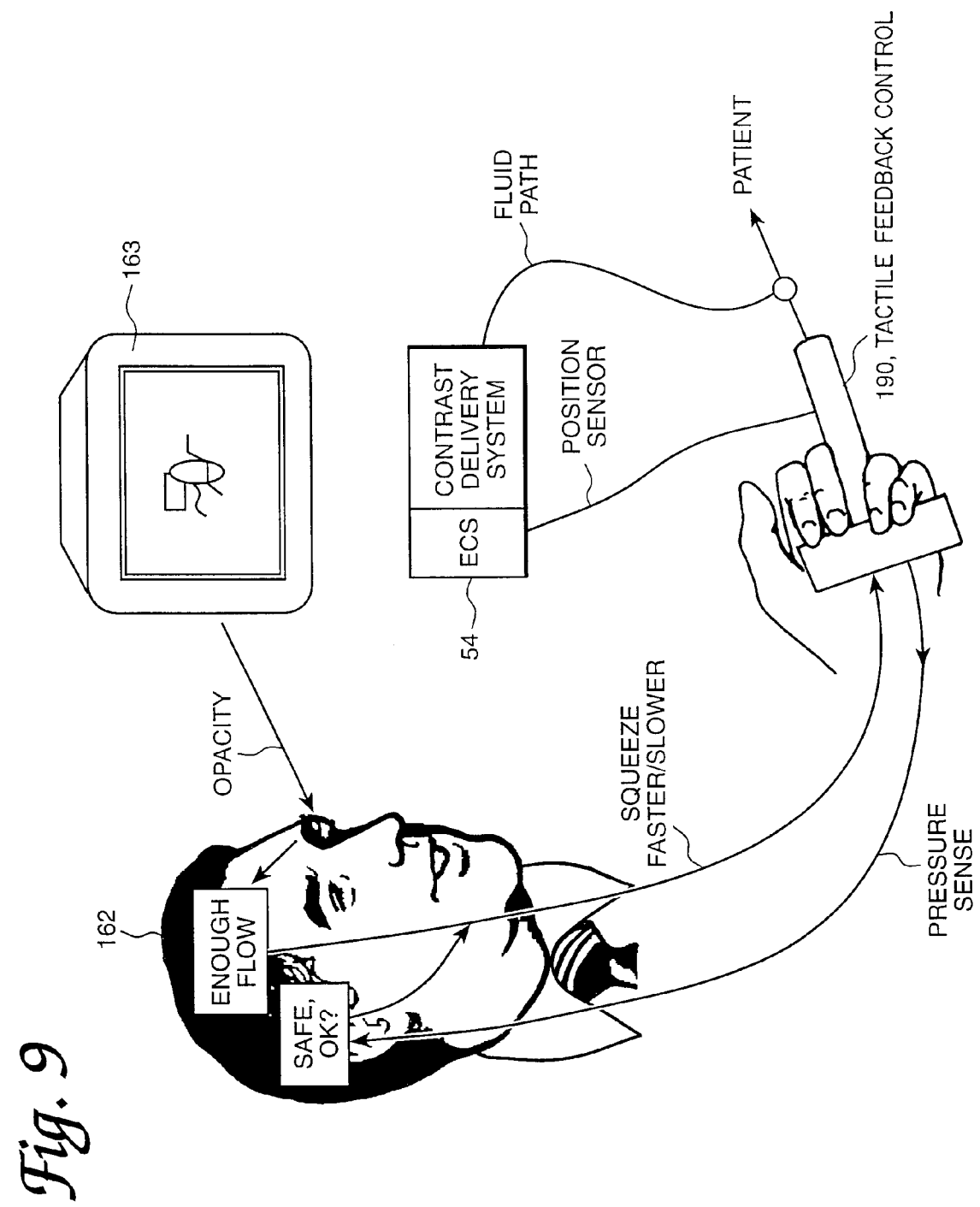
FIG. 9 illustrates an embodiment of the present invention which incorporates a Tactile Feedback Control (TFC) unit which allows the system operator to adjust injection parameters based on this sensor as well as the resulting image. The TFC is in fluid communication with the fluid being injected.

FIG. 9 illustrates the embodiment of the present invention disclosed in FIG. 8, wherein the operator 162 is able to adjust flow rate via the Tactile Feedback Control unit (TFC) 174. The operator is able to feel the actual pressure used during the injection procedure and is able to adjust flow rate based on the resultant image displayed on the video monitor 163. The system incorporates pressure limitations to prevent patient injury. This system is similar to that shown in FIG. 7, except that the operator views the region of interest, and pushes on the TFC in proportion to the amount of contrast media desired to be injected based on the resulting image. In addition to the feedback via the video image, the doctor receives pressure feedback via the hand held unit. Doctor are familiar with this type of feedback because it is similar to the situation encountered when a powered fluid delivery system is not used. This increases their confidence when using the system in critical areas such as coronary vessels. As the operators gain confidence in the safety and reliability of the system, it will be possible for the system operation to be more automatic as shown in FIGS. 2, 4, 5, or 7.

Figure 10A:
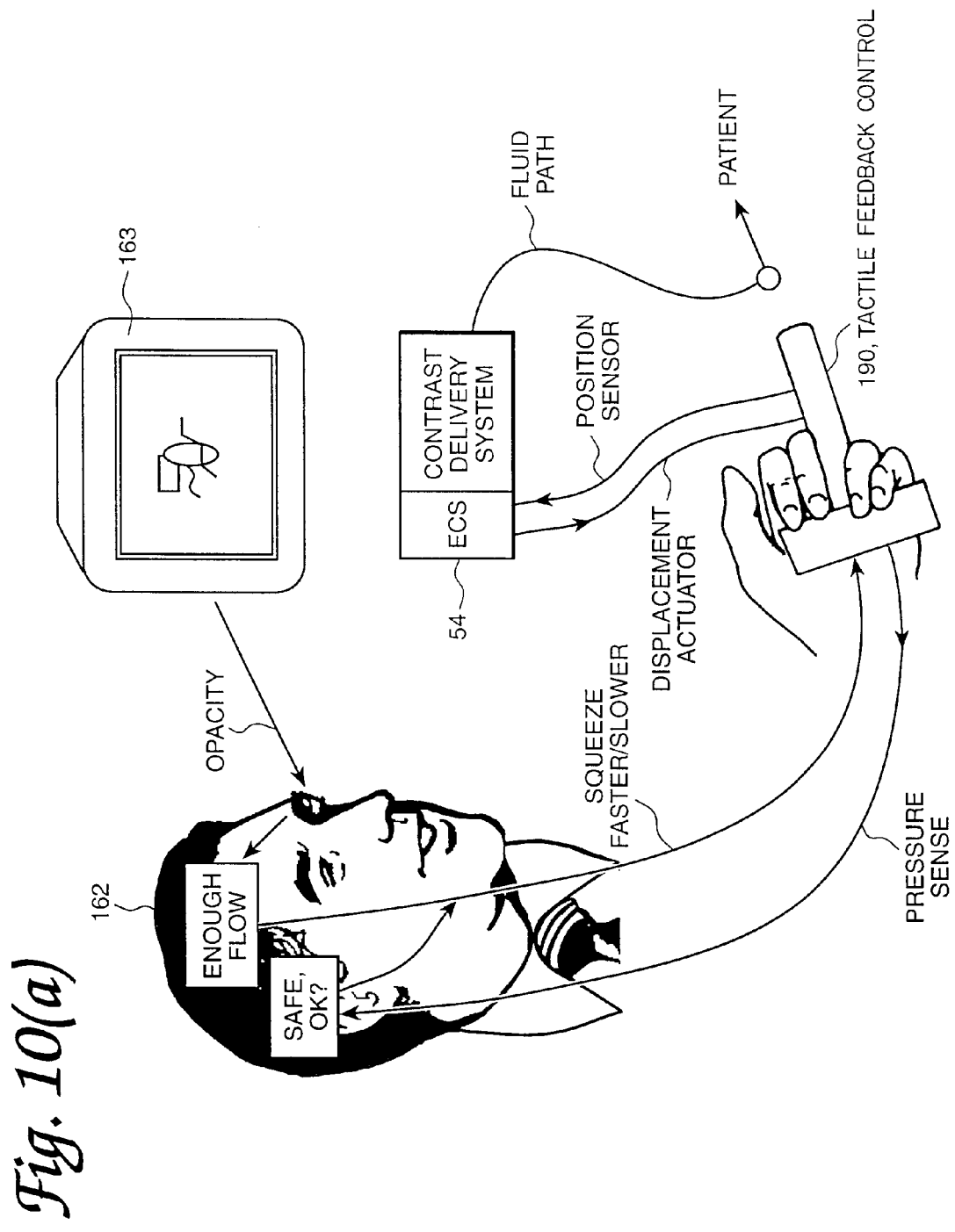
FIG. 10a illustrates an embodiment of the present invention which incorporates a Tactile Feedback Control (TFC) unit which allows the system operator to adjust injection parameters based on this sensor as well as the resulting image. The TFC is not in fluid communication with the fluid being injected.

FIG. 10a illustrates use of another embodiment of the present invention wherein the ECS uses signals generated in the TFC 190 to determine a proportionate amount of fluid to be injected into the patient. In this embodiment, displacement is proportional to the actual amount of fluid delivered and the TFC is not in fluid communication with the fluid being delivered.

FIG. 10b shows more details of the TFC unit disclosed in FIG. 10a which would eliminate the fluid path connection between the TFC and the actual fluid being injected. It consists of a plunger 200 with a threaded section 201. The base consists of an outside case 205, a pressure sensor 207 attached to the case, and a motor 209, the base of which is attached through the pressure sensor 207 to the base of the case 205. The shaft of the motor is connected to a threaded rod 210. The plunger 200 freely slides back and forth with respect to the base. The plunger 200 cannot rotate with respect to the base. On the end of the plunger nearest the base is a threaded section 201. As the threaded rod 210 rotates, the plunger 200 is moved in or out, depending upon the direction of rotation. If desired, a linear potentiometer may be connected to the plunger to provide a resistance proportional to the position of the plunger in the base for measurement by the ECS.

To the doctor, the TFC functions as a syringe. When the doctor pushes on the plunger 200, he generates a force which is sensed by the force sensor 207. The output of this sensor is proportional to the force applied by the doctor. Various types of force sensors may be used such as, for example, a piezoelectric film or a stiff spring with a linear displacement potentiometer. The ECS receives the pressure signal, and generates a proportional pressure in the contrast delivery system (CDS). As the fluid is delivered by the CDS, the ECS energizes the motor 209 which rotates the threaded cylinder 210. Thus the plunger moves toward the base as the fluid is being delivered to the patient, and the doctor is sensing a resistance force which is proportional to the pressure required to deliver the fluid.

The TFC of FIG. 10b provides several benefits. It is completely reusable, because it may be either sterilized or simply covered by a bag. The fluid path is simplified, and therefore less expensive, easier to install, fill and assure the removal of air. The TFC can be much farther from the patient thereby also allowing the doctor or operator to be farther from the radiation field and receive less X-ray radiation. Both the ratios between the applied force and pressure in the CDS and between flow rate and displacement rate can be varied electronically, whereas in the previously described TFC, the force was set by the diameter of the disposable syringe.

In either of the TFC embodiments shown in FIGS. 8 and 10b, it is possible to operate in several modes. In the preferred mode, the displacement of the TFC is proportional to the volume of fluid being injected, and the rate of fluid injection is proportional to the rate at which the plunger of the TFC is displaced. A second mode is described with a control system which is similar to that found in a variable speed drill. In this system, the flow rate of the injection is proportional to the displacement of the TFC. This mode is not the primary one but may be preferred by some operators.

The simplest algorithm assumes a linear relationship between the TFC displacement and the volume injected or the flow rate being injected. Other relationships are possible. Some examples are given in FIGS. 11a–d. In the TFC of FIG. 8, the syringe is actually connected to the fluid line therefore the pressure in the TFC is the same as that at the injection, and the force felt by the operator is controlled by the diameter of the syringe. In the electronically actuated TFC the relationship between input at the TFC and output from the CDS can follow any of the relationships of FIG. 11 or many others as well. The relationship may be different for different operators. A strong man is likely to prefer a different relationship than a smaller woman. In a preferred embodiment, the system would be configured according to individual preferences and the operator could simply enter their name and password to set the desired preferences.

Figure 11A:
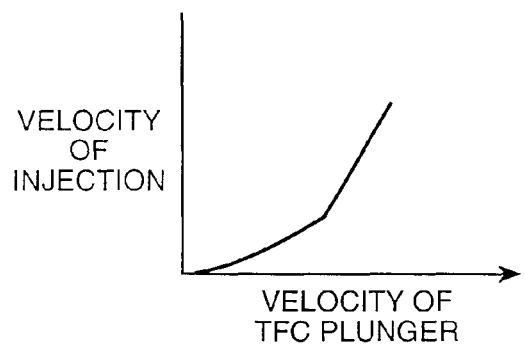
FIGS. 11a–d illustrate various relationships between TFC inputs and contrast delivery system actions which an operator could select with the system.
Figure 11B:
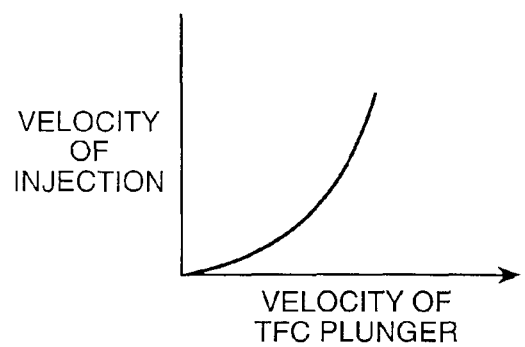
Figure 11C:
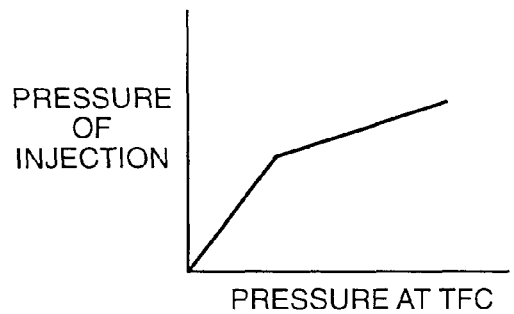
Figure 11D:
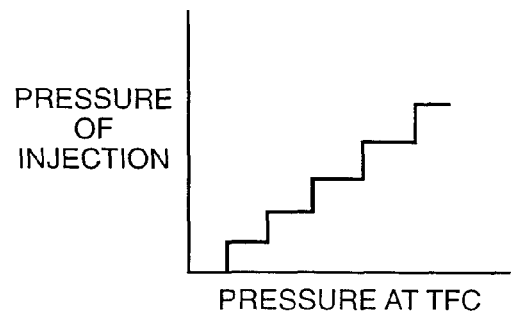

The example in FIG. 11d describes a relationship that might be used to inflate a balloon for angioplasty. The pressure in the CDS would be increased in steps as the pressure in the TFC is increased.

Another capability of this embodiment is to synchronize the CDS with an electrocardiogram signal. Present injectors can be programmed to inject a specific volume at specific flow rate and position relative to a marker on an electrocardiogram such as, for example, the R wave. These systems are preferred by some, but do not have the confidence of others. It is not possible for an operator to manually synchronize with the electrocardiogram signal, so they inject by hand at a constant rate. This practice results in a waste of contrast media because the fluid flows into vessels which are not being studied. A benefit of the TFC is that the operator now has the instantaneous control of the injection with feedback on pressure and flow rate. The CDS is able to synchronize with the electrocardiogram thus minimizing the use of contrast media thus saving cost and dose to the patient.

The selected exemplary embodiments of the TFC units set forth above describe two design choices for the TFC. It is contemplated that various substitutions and modifications could be made to accomplish the results of the selected designs. The claims are in no way limited to these preferred embodiments.

Figure 12:
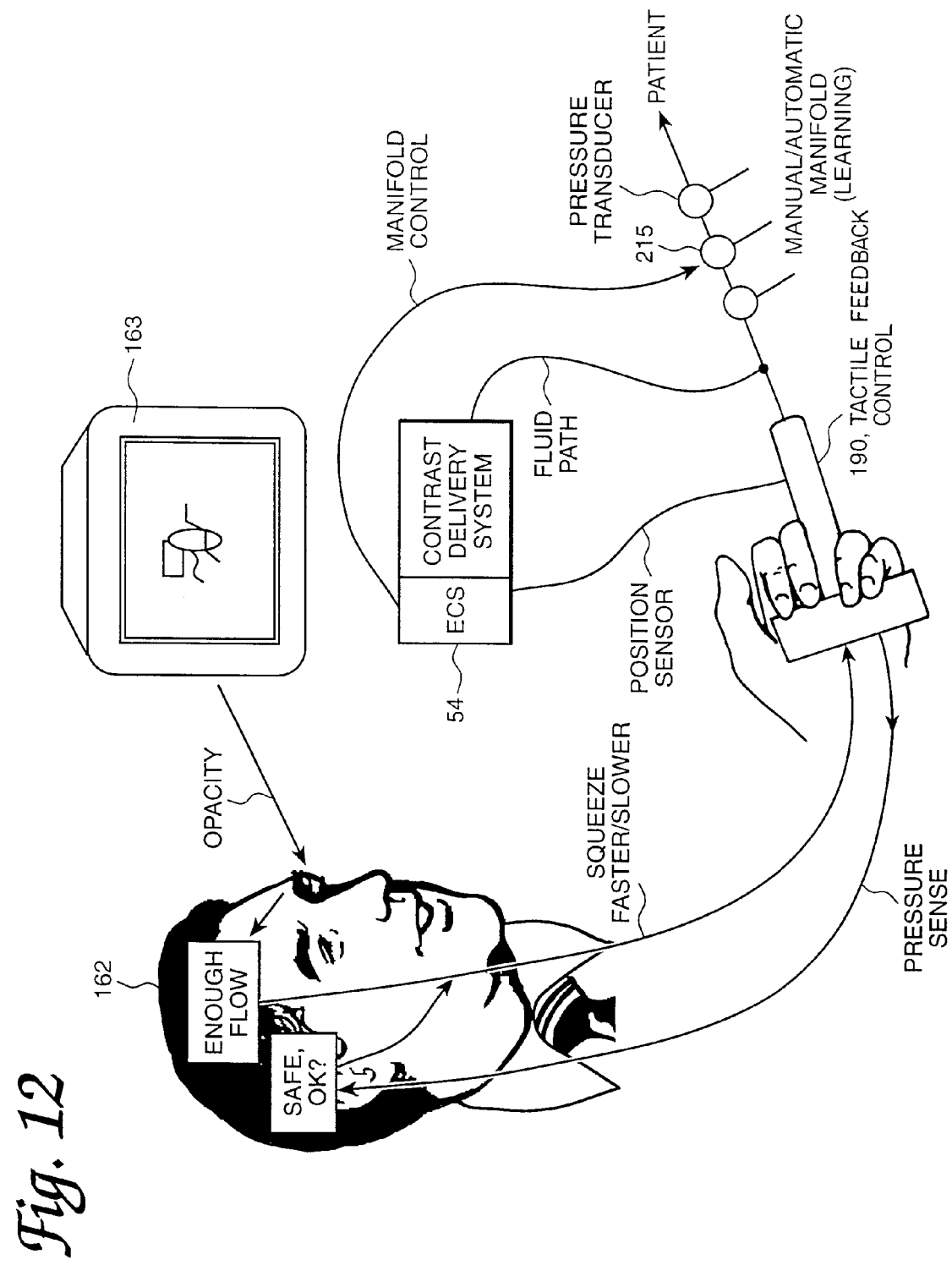
FIG. 12 illustrates disposable manifolds operated by electronic solenoids or motors which are designed for use with the present invention during cardiology.

FIG. 12 illustrates an enhanced version of the system which is designed for cardiology. In CT, MR and many angiographic procedures, the contrast injector does not share the fluid path to the patient with any other devices. In cardiology, the situation is different. Presently, cardiologists use a manually activated manifold with several three-way or four-way valves. These valves are used so a single fluid line can measure pressure, perform scout injections, and provide various fluids during manipulation of the catheter to get it into the proper vessel. In this embodiment of the invention, the disposable manifolds 215 are operated by electronic solenoids or motors controlled by the ECS. Thus the whole sequence of the procedure is automated to a great extent.

Figure 13:
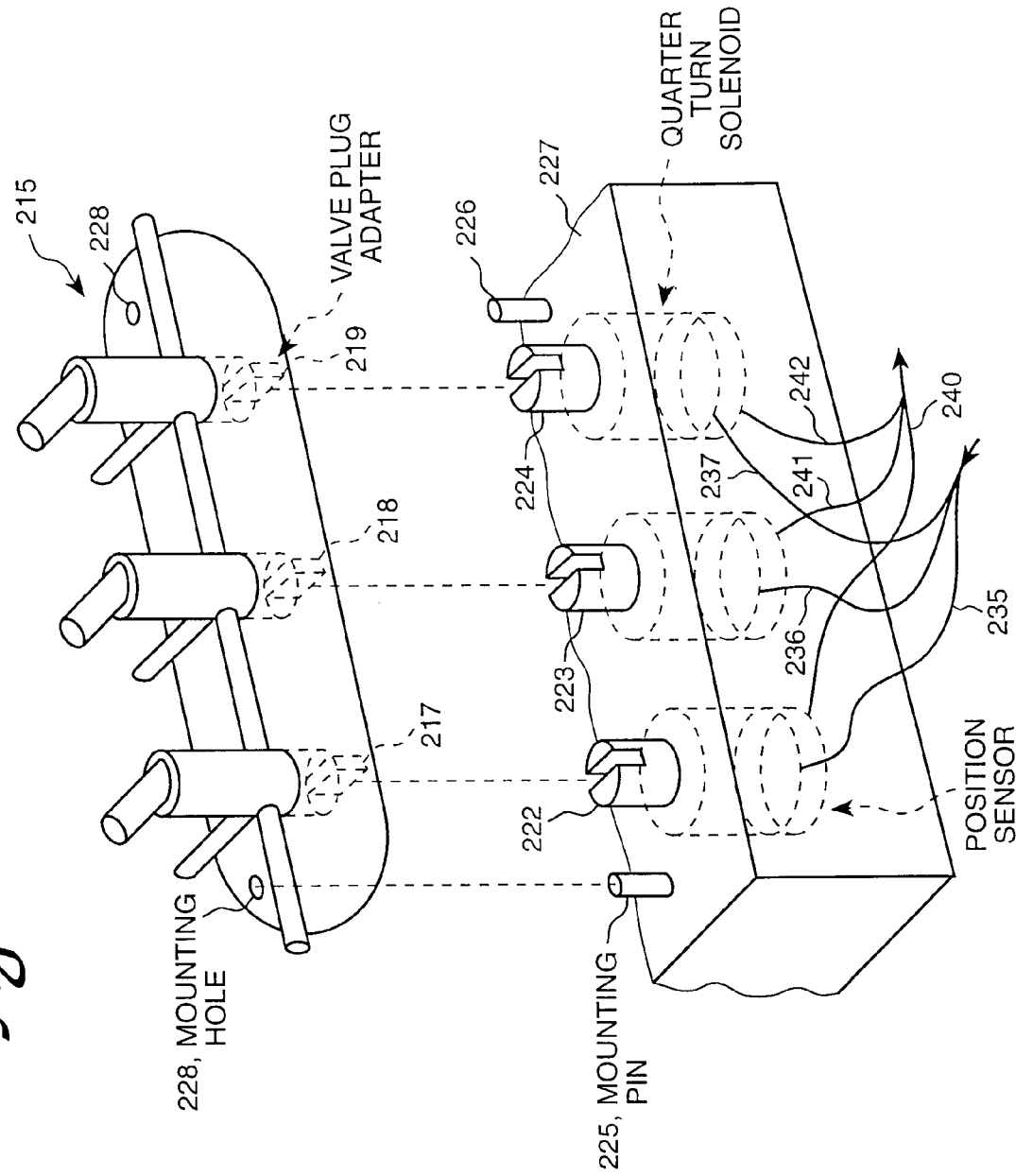
FIG. 13 illustrates a manifold for use with the present invention during cardiology procedures.

FIG. 13 provides additional detail. A sterile disposable manifold 215 is shown and is similar to those manufactured by North American Instrument Corporation of Glen Falls, N.Y. The only difference is that manifold 215 includes valve adaptor plugs 217, 218, 219 which mate with slots in quarter-turn solenoid heads 221, 222, 223. Although numerous mating geometries are possible, there is a safety advantage if mating may be accomplished in a single orientation. In the preferred embodiment described in FIG. 13, a single orientation is assured by having slots located in the solenoid heads which are more narrow on one end than the other. Mounting pins 225 and 226 located on the solenoid mounting case 227 mate with mounting holes 228, 229 on the disposable manifold 215 to secure the manifold to the solenoid mounting case.

The ECS controls the position of the quarter-turn solenoids 231, 232, 233 via control lines 235, 236, 237. The quarter-turn solenoids are simple electro-mechanical devices which rotate ninety-degrees each time they are energized. In the described system, the solenoids need only rotate in a single direction because three successive energizations is the same as moving one quarter-turn in the opposite direction. It is also important that the system is capable of determining the position of the manifolds to ensure that this information is available when power is first turned on and also to verify that the valves move as commanded. Simple position sensors are utilized for this purpose and send signals to the ECS via sense lines 240, 241, and 242. In a preferred embodiment the sensors are optical encoders for simplicity and reliability.

Figure 14:
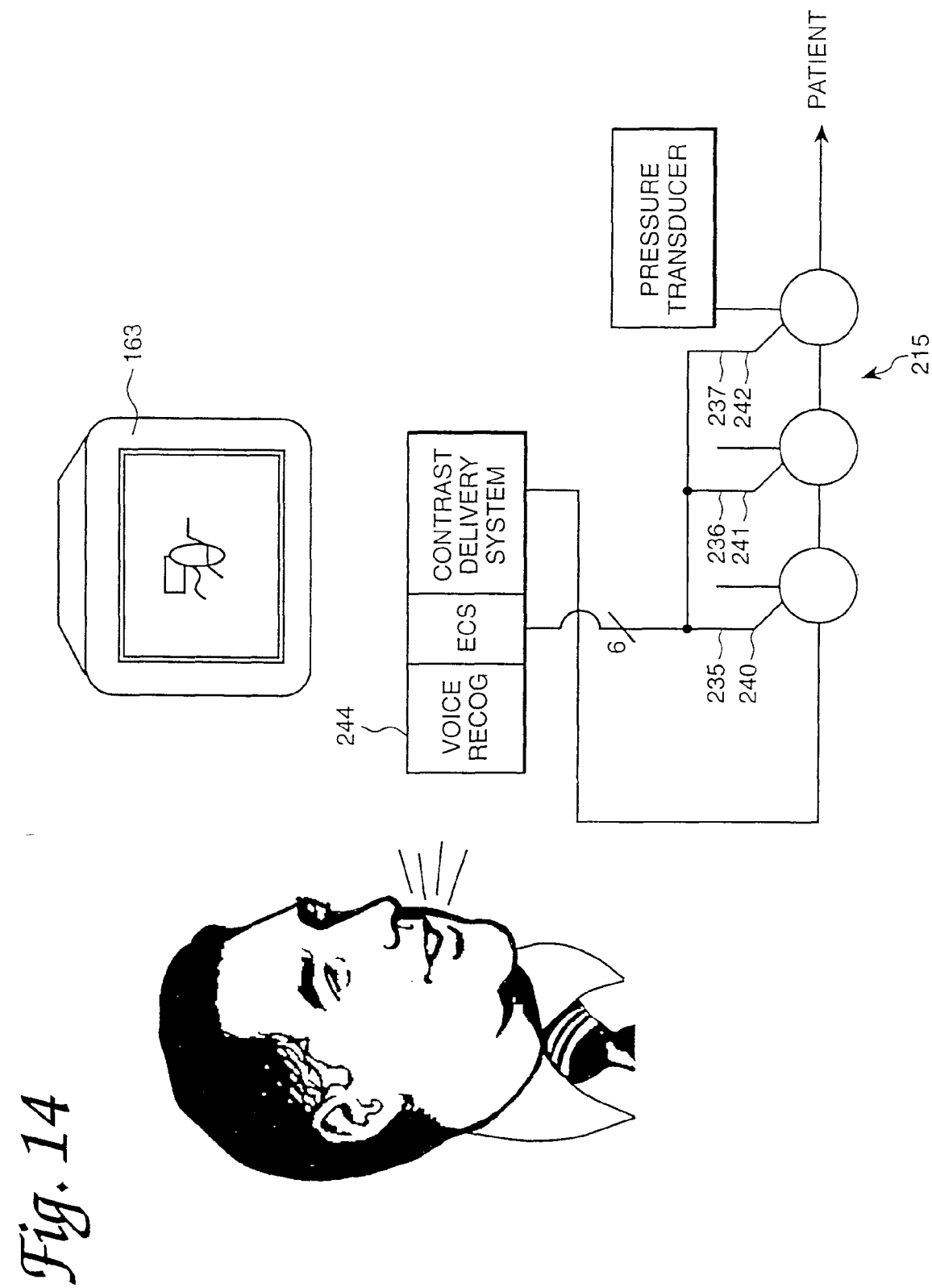
FIG. 14 illustrates a system by which the manifold illustrated in FIG. 13 is voice-activated.

A doctor may activate the manifold via any type of remote control such as hand switches, foot switches or verbally with the aid of voice recognition equipment. This last possibility is illustrated by FIG. 14. There is a significant benefit in the ability of the doctor to activate a control for example by simply stating, "measure pressure," and have all the valves move to the proper position. Alternatively, the doctor could say, "scout injection," and the ECS operating in conjunction with the voice recognition equipment 244 would set the valves to the proper position for that function. This would eliminate many of the separate actions which a doctor currently is required to perform in using currently available systems. An additional advantage is that a doctor using the system is able to operate the equipment while being physically further from the patient thus being able to avoid the damaging effects of the x-ray radiation.

In those embodiments where the operator is in the feedback loop, additional feedback relating to system operation may be provided to enhance system performance. For example, the operator may receive audio feedback related to operational characteristics such as speed, volume injected or pressure. Tone of an audible signal could be used such that a higher pitch would indicate a higher speed, greater volume, or greater pressure. Alternatively, an audible click could be used to indicate injection of each milliliter of fluid or the click repetition rate could be proportional to the pressure. Audible feedback allows the operator to receive this information while the operator continues to monitor the patient or the image on the display 163. In a preferred embodiment, the audio feedback is transmitted to the operator via an ear phone which is either hard wired or battery powered to eliminate an additional distraction in a busy room and to avoid the possibility of the patient becoming alarmed as a result of the audio signal.

Alternatively, the additional feedback could be displayed on the video monitor 163 along with the patient image. Providing the additional feedback visually avoids the possible distraction of others and is particularly useful if it can be displayed without distracting the operator from viewing the patient image. One method of simultaneous display is the use of numbers on the monitor which indicate flow rate. A bar graph or a syringe outline which empties as the fluid is injected are other options.

Although the present invention has been described in terms of preferred embodiments, the present description is given by way of example and is not intended to be limiting to the scope of the invention described and claimed herein.

What is claimed is:

1. An injection system for injecting fluid into a patient, the injection system comprising:
   a fluid delivery apparatus;
   a fluid path structured to be disposed between the fluid delivery apparatus and the patient;
   a control unit in communication with and operable to control the fluid delivery apparatus; and a control mechanism in communication with the control unit, the control mechanism comprising a tactile feedback unit and a sensor that generates and sends a signal to the control unit, whereby the control unit controls the injection of fluid into the patient in proportion to the signal.

2. The injection system of claim 1 wherein the sensor comprises a force sensor.

3. The injection system of claim 1 wherein the control mechanism is in fluid communication with the fluid path.

4. The injection system of claim 3 wherein the pressure generated by the fluid in the fluid path is communicated to the control mechanism.

5. The injection system of claim 1 wherein the tactile feedback unit comprises an actuator mechanism in communication with the sensor.

6. The injection system of claim 5 wherein the sensor senses movement of the actuator mechanism by an operator.

7. The injection system of claim 6 wherein the signal generated by the sensor is proportional to the movement of the actuator mechanism.

8. The injection system of claim 6 wherein the volume of injected fluid is proportional to the displacement of the actuator mechanism.

9. The injection system of claim 6 wherein the flow rate of injected fluid is proportional to the rate of displacement of the actuator mechanism.

10. The injection system of claim 6 wherein the flow rate of injected fluid is proportional to the displacement of the actuator mechanism.

11. The injection system of claim 5 wherein the actuator mechanism comprises a plunger.

12. The injection system of claim 5 wherein the flow rate of the fluid is controlled by the control unit.

13. The injection system of claim 1 wherein the sensor comprises a potentiometer.

14. The injection system of claim 1 wherein the control mechanism is reusable.

15. The injection system of claim 1 wherein the proportional relationship between the signal and the injection of fluid is a substantially linear relationship.

16. The injection system of claim 1, wherein the sensor is an integrated element of the control mechanism.

17. The injection system of claim 1, wherein the tactile feedback unit comprises a syringe and the sensor is disposed on a cradle coupled to the syringe.

18. The injection system of claim 1 wherein the sensor is configured to sense the pressure within the control mechanism.

19. The injection system of claim 1 wherein the sensor is configured to sense the pressure within the fluid path.

20. An injection system for injecting fluid into a patient, the injection system comprising:

a fluid delivery apparatus;

a fluid path structured to be disposed between the fluid delivery apparatus and the patient;

a manifold disposed in the fluid path between the fluid delivery apparatus and the patient;

a control unit in communication with and operable to control the fluid delivery apparatus; and a control mechanism in communication with the control unit, the control mechanism comprising a tactile feedback unit and a sensor that generates and sends a signal to the control unit, whereby the control unit controls the injection of fluid into the patient in proportion to the signal.

21. The injection system of claim 20 wherein the sensor comprises a force sensor.

22. The injection system of claim 20 wherein the control mechanism is in fluid communication with the fluid path.

23. The injection system of claim 22 wherein the pressure generated by the fluid in the fluid path is communicated to the control mechanism.

24. The injection system of claim 20 wherein the tactile feedback unit comprises an actuator mechanism in communication with the sensor.

25. The injection system of claim 24 wherein the sensor senses movement of the actuator mechanism by an operator.

26. The injection system of claim 25 wherein the signal generated by the sensor is proportional to the movement of the actuator mechanism.

27. The injection system of claim 25 wherein the volume of injected fluid is proportional to the displacement of the actuator mechanism.

28. The injection system of claim 25 wherein the flow rate of injected fluid is proportional to the rate of displacement of the actuator mechanism.

29. The injection system of claim 25 wherein the flow rate of injected fluid is proportional to the displacement of the actuator mechanism.

30. The injection system of claim 24 wherein the actuator mechanism comprises a plunger.

31. The injection system of claim 24 wherein the flow rate of the fluid is controlled by the control unit.

32. The injection system of claim 20 wherein the sensor comprises a potentiometer.

33. The injection system of claim 20 wherein the control mechanism is reusable.

34. The injection system of claim 20 wherein the proportional relationship between the signal and the injection of fluid is a substantially linear relationship.

35. The injection system of claim 20 wherein the control unit is in communication with and is operable to control the manifold.

36. The injection system of claim 20 wherein the manifold is manually operated.

37. The injection system of claim 20 wherein the manifold is power activated.

38. The injection system of claim 20 wherein the sensor is an integrated element of the control mechanism.

39. The injection system of claim 20 wherein the tactile feedback unit comprises a syringe and the sensor is disposed on a cradle coupled to the syringe.

40. An injection system for injecting fluid into a patient, the injection system comprising:

a fluid delivery apparatus;

a fluid path structured to be disposed between the fluid delivery apparatus and the patient;

a control unit in communication with and operable to control the fluid delivery apparatus; and a control mechanism in communication with the control unit, the control mechanism comprising a sensor that generates and sends a signal to the control unit, whereby the control unit is programmed to control the injection of fluid into the patient in proportion to the signal, wherein the control mechanism further comprises a syringe, the sensor being formed on a cradle coupled to the syringe, and an actuator mechanism in communication with the sensor, the sensor senses movement of the actuator mechanism by an operator, and the signal generated by the sensor is proportional to the movement of the actuator mechanism.

41. The injection system of claim 40 wherein the control mechanism is hand-operated.

42. The injection system of claim 40 wherein the control mechanism is in fluid communication with the fluid path.

43. The injection system of claim 40 wherein the actuator mechanism comprises a plunger.

44. The injection system of claim 40 wherein the sensor comprises a potentiometer.

45. The injection system of claim 40 wherein the flow rate of the fluid is controlled by the control unit.

46. The injection system of claim 40 wherein the control mechanism is reusable.

47. The injection system of claim 40 wherein the volume of injected fluid is proportional to the displacement of the actuator mechanism.

48. The injection system of claim 40 wherein the flow rate of injected fluid is proportional to the rate of displacement of the actuator mechanism.

49. The injection system of claim 40 wherein the flow rate of injected fluid is proportional to the displacement of the actuator mechanism.

50. The injection system of claim 40 wherein the proportional relationship between the signal and the injection of fluid is a substantially linear relationship.

51. The injection system of claim 40 wherein the pressure generated by the fluid in the fluid path is communicated to the control mechanism.

52. The injection system of claim 40, further comprising a manifold disposed in the fluid path between the fluid delivery apparatus and the patient.

53. The injection system of claim 52 wherein the control unit is in communication with and is operable to control the manifold.

54. The injection system of claim 52 wherein the manifold is manually operated.

55. The injection system of claim 52 wherein the control mechanism is in fluid communication with the fluid pat.

56. The injection system of claim 52 wherein the manifold is power activated.

57. The injection system of claim 40 wherein the sensor is an integrated element of the control mechanism.

58. The injection system of claim 40 wherein the sensor is configured to sense the pressure within the control mechanism.

59. The injection system of claim 40 wherein the sensor is configured to sense the pressure within the fluid path.

\* \* \* \* \*